United States Patent
Palmaz

(10) Patent No.: US 9,272,077 B2
(45) Date of Patent: Mar. 1, 2016

(54) IMPLANTABLE MATERIALS HAVING ENGINEERED SURFACES AND METHOD OF MAKING SAME

(71) Applicant: PALMAZ SCIENTIFIC, INC., Dallas, TX (US)

(72) Inventor: Julio C. Palmaz, Napa, CA (US)

(73) Assignee: Palmaz Scientific, Inc., Fremont, CA (US)

( * ) Notice: Subject to any disclaimer, the term of this patent is extended or adjusted under 35 U.S.C. 154(b) by 0 days.

(21) Appl. No.: 14/219,924

(22) Filed: Mar. 19, 2014

(65) Prior Publication Data

US 2014/0294910 A1 Oct. 2, 2014

Related U.S. Application Data

(60) Division of application No. 13/107,510, filed on May 13, 2011, now Pat. No. 8,679,517, which is a continuation-in-part of application No. 12/428,981, filed on Apr. 23, 2009, now Pat. No. 8,268,340, which is a continuation-in-part of application No. 11/091,669, filed on Mar. 28, 2005, now Pat. No. 8,147,859, which is a continuation of application No. PCT/US03/30383, filed on Sep. 26, 2003.

(60) Provisional application No. 60/414,031, filed on Sep. 26, 2002.

(51) Int. Cl.
*A61L 31/16* (2006.01)
*A61F 2/00* (2006.01)
*A61F 2/02* (2006.01)

(52) U.S. Cl.
CPC ............... *A61L 31/16* (2013.01); *A61F 2/0077* (2013.01); *A61F 2/02* (2013.01)

(58) Field of Classification Search
CPC ........................... A61F 2/07; A61F 2002/0086
See application file for complete search history.

(56) References Cited

U.S. PATENT DOCUMENTS

| | | | |
|---|---|---|---|
| 4,657,544 A | 4/1987 | Pinchuk | 623/1 |
| 5,133,845 A | 7/1992 | Vallana et al. | 204/192.15 |
| 5,207,709 A | 5/1993 | Picha | 623/11 |
| 5,278,063 A | 1/1994 | Hubbell et al. | 435/240.243 |

(Continued)

FOREIGN PATENT DOCUMENTS

| | | | | |
|---|---|---|---|---|
| DE | 0 603 959 | 6/1994 | | A61F 2/06 |
| DE | 199 16 086 | 10/1999 | | A61F 2/04 |

(Continued)

OTHER PUBLICATIONS

European Search Report issued in corresponding foreign application, pp. 1-7 (Oct. 1, 2014).

(Continued)

*Primary Examiner* — Rosanne Kosson
(74) *Attorney, Agent, or Firm* — David G. Rosenbaum; J. Peter Paredes; Rosenbaum IP, P.C.

(57) ABSTRACT

An implantable biocompatible material includes one or more vacuum deposited layers of biocompatible materials deposited upon a biocompatible base material. At least a top most vacuum deposited layer includes a homogeneous molecular pattern of distribution along the surface thereof and comprises a patterned array of geometric physiologically functional features.

9 Claims, 11 Drawing Sheets

(56) References Cited

U.S. PATENT DOCUMENTS

| | | | |
|---|---|---|---|
| 5,370,684 A | 12/1994 | Vallana et al. | 623/1 |
| 5,387,247 A | 2/1995 | Vallana et al. | 623/66 |
| 5,423,885 A | 6/1995 | Williams | 623/1 |
| 5,510,628 A | 4/1996 | Georger, Jr. et al. | 257/32 |
| 5,607,463 A | 3/1997 | Schwartz et al. | 623/1 |
| 5,649,951 A | 7/1997 | Davidson | 606/198 |
| 5,690,670 A | 11/1997 | Davidson | 606/198 |
| 5,725,573 A | 3/1998 | Dearnaley et al. | 623/2 |
| 5,733,303 A | 3/1998 | Israel et al. | 606/198 |
| 5,735,896 A | 4/1998 | Amon et al. | 623/11 |
| 5,782,908 A | 7/1998 | Cahalan et al. | 623/1 |
| 5,843,289 A | 12/1998 | Lee et al. | 204/192.3 |
| 5,849,206 A | 12/1998 | Amon et al. | 216/63 |
| 5,891,507 A | 4/1999 | Jayaraman | 427/2.25 |
| 5,895,419 A | 4/1999 | Tweden et al. | 623/2 |
| 5,897,911 A | 4/1999 | Loeffler | 427/2.25 |
| 5,932,299 A | 8/1999 | Katoot | 427/508 |
| 5,955,588 A | 9/1999 | Tsang et al. | 536/21 |
| 6,001,622 A | 12/1999 | Dedhar et al. | 435/194 |
| 6,027,526 A | 2/2000 | Limon et al. | 623/1 |
| 6,077,413 A | 6/2000 | Hafeli et al. | 205/170 |
| 6,086,773 A | 7/2000 | Dufresne et al. | 216/8 |
| 6,103,320 A | 8/2000 | Matsumoto et al. | 427/535 |
| 6,140,127 A | 10/2000 | Sprague | 435/395 |
| 6,143,370 A | 11/2000 | Panagiotou et al. | 427/422 |
| RE36,991 E | 12/2000 | Yamamoto et al. | 204/403 |
| 6,183,255 B1 | 2/2001 | Oshida | 433/201.1 |
| 6,190,404 B1 * | 2/2001 | Palmaz | A61F 2/91 623/1.15 |
| 6,192,944 B1 | 2/2001 | Greenhalgh | 139/425 |
| 6,207,536 B1 | 3/2001 | Matsumoto et al. | 438/478 |
| 6,253,441 B1 | 7/2001 | Wheat et al. | 29/527.2 |
| 6,258,121 B1 | 7/2001 | Yang et al. | 623/1.46 |
| 6,274,014 B1 | 8/2001 | Matsumoto et al. | 204/298.11 |
| 6,280,467 B1 | 8/2001 | Leonhardt | 623/1.16 |
| 6,325,825 B1 | 12/2001 | Kula et al. | 623/1.3 |
| 6,334,868 B1 | 1/2002 | Ham | 623/1.13 |
| 6,379,383 B1 * | 4/2002 | Palmaz | A61F 2/82 623/1.49 |
| 6,432,128 B1 | 8/2002 | Wallace et al. | 623/1.11 |
| 6,514,261 B1 | 2/2003 | Randall et al. | 606/108 |
| 6,520,923 B1 | 2/2003 | Jalisi | 600/585 |
| 6,527,919 B1 | 3/2003 | Roth | 204/192.15 |
| 6,527,938 B2 | 3/2003 | Bales et al. | 205/229 |
| 6,533,905 B2 | 3/2003 | Johnson et al. | 204/192.15 |
| 6,537,310 B1 | 3/2003 | Palmaz et al. | 623/1.13 |
| 6,652,579 B1 | 11/2003 | Cox et al. | 623/1.34 |
| 6,689,473 B2 | 2/2004 | Guire et al. | 428/412 |
| 6,849,085 B2 | 2/2005 | Marton | 623/1.13 |
| 8,147,859 B2 * | 4/2012 | Palmaz | A61F 2/00 424/423 |
| 8,702,790 B2 | 4/2014 | Pelton et al. | 623/1.18 |
| 8,715,339 B2 | 5/2014 | Atanasoska et al. | 623/1.39 |
| 8,715,340 B2 | 5/2014 | Rudakov et al. | 623/1.39 |
| 8,715,771 B2 | 5/2014 | Orosa et al. | 427/2.24 |
| 8,739,727 B2 | 6/2014 | Austin et al. | 118/211 |
| 8,758,636 B2 | 6/2014 | Quandt et al. | 216/36 |
| 2001/0001834 A1 * | 5/2001 | Palmaz | A61F 2/82 623/1.15 |
| 2001/0039454 A1 | 11/2001 | Ricci et al. | 623/23.5 |
| 2002/0016623 A1 | 2/2002 | Kula et al. | 623/1.11 |
| 2002/0017503 A1 | 2/2002 | Banas et al. | 219/69.11 |
| 2002/0156522 A1 | 10/2002 | Ivancev et al. | 623/1.13 |
| 2003/0028244 A1 | 2/2003 | Bates et al. | 623/1.15 |
| 2003/0028246 A1 | 2/2003 | Palmaz et al. | 623/1.49 |
| 2003/0130718 A1 | 7/2003 | Palmas et al. | 330/254 |
| 2004/0014253 A1 | 1/2004 | Gupta et al. | 438/48 |
| 2005/0033418 A1 | 2/2005 | Banas et al. | 623/1.49 |
| 2005/0055085 A1 | 3/2005 | Rivron et al. | 623/1.39 |
| 2005/0102036 A1 | 5/2005 | Bartec et al. | 623/23.76 |
| 2005/0119723 A1 | 6/2005 | Peacock, III | 623/1.15 |
| 2005/0232968 A1 | 10/2005 | Palmaz et al. | 424/423 |
| 2006/0178751 A1 | 8/2006 | Despres, III et al. | 623/23.5 |
| 2007/0225823 A1 | 9/2007 | Hawkins et al. | 623/23.51 |
| 2007/0250156 A1 | 10/2007 | Palmaz | 623/1.39 |
| 2008/0183276 A1 | 7/2008 | Melder | 623/1.15 |
| 2009/0304772 A1 | 12/2009 | Choubey et al. | 424/423 |
| 2009/0311297 A1 | 12/2009 | Hontsu et al. | 424/422 |
| 2010/0227372 A1 | 9/2010 | Bilek et al. | 435/180 |
| 2014/0128901 A1 | 5/2014 | Kang et al. | 606/194 |

FOREIGN PATENT DOCUMENTS

| | | | |
|---|---|---|---|
| EP | 0 701 803 | 1/1995 | A61F 2/30 |
| EP | 0 747 069 | 12/1996 | A61L 29/00 |
| EP | 0 815 806 | 6/1997 | A61F 2/06 |
| EP | 0 850 604 | 1/1998 | A61F 2/06 |
| EP | 0 875 217 | 11/1998 | A61F 2/06 |
| EP | 1 028 672 | 6/2005 | A61F 2/06 |
| EP | 0 895 762 | 2/2008 | A61F 2/90 |
| JP | 07-284527 | 10/1995 | A61F 27/00 |
| JP | 09-225021 | 2/1997 | A61L 27/00 |
| JP | 63-502405 | 9/1998 | A61L 2/06 |
| JP | 2001-294411 | 10/2001 | C01B 25/32 |
| JP | 2002-017847 | 1/2002 | A61L 27/00 |
| WO | WO 95/12472 | 5/1995 | B23K 26/02 |
| WO | WO 98/45506 | 10/1998 | C25D 7/04 |
| WO | WO 99/23977 | 5/1999 | A61F 2/06 |
| WO | WO 01/35865 | 5/2001 | A61F 2/06 |
| WO | WO 01/68158 | 9/2001 | A61L 27/08 |
| WO | WO 01/74274 | 10/2001 | A61F 2/06 |
| WO | WO 01/76525 | 10/2001 | A61F 2/06 |
| WO | WO 01/87371 | 11/2001 | A61L 27/42 |
| WO | WO 01/89420 | 11/2001 | A61F 2/06 |
| WO | WO 2004/028347 | 4/2004 | |
| WO | WO 2012/154/862 | 11/2012 | A61F 2/01 |
| WO | WO 2014/070404 | 5/2014 | A61F 2/91 |
| WO | WO 2014/070532 | 5/2014 | A61F 2/91 |

OTHER PUBLICATIONS

Bunshah, R.F., "3 Mechanical properties of thin films 3.1 Mechanical properties of PVD films" *Vacuum* 27(4): 353-362 (1977).

Carney, C., et al., "Establishing the relationship between process, structure, and properties of TiN films deposited by electron cyclotron resonance assisted reactive sputtering. I. Variations in hardness and roughness as a function of process parameters" *J. Vac. Sci. Technol. A* 17(5): 2850-2858 (1999).

Carney, C., et al., "Establishing the relationship between process, structure, and properties of titanium nitride films deposited by electron cyclotron resonance assisted reactive sputtering. II. A process model" *J. Vac. Sci. Technol. A* 17(5): 2859-2868 (1999).

Chen, C., et al. "Reports: Geometric Control of Cell Life and Death" *Science* 276(5317): 1425-1428 (1977).

Chiu, K.F., "The control of film stress using ionized magnetron sputter deposition" *Thin Solid Films* 343-344: 39-42 (1999).

Choubey, Animesh, "Grain Boundary Etched 316L Stainless Steel Surfaces for Cardiovascular Stents, Dissertation".

Chu, P.K., et al., "Plasma-surface modification of biomaterials," *Materials Science and Engineering* R 36: 143-206 (2002).

Dahlgren, S.D., et al., "Microstructure of sputter-deposited 304L stainless steel" *The Journal of Vacuum Science and Technology* 7(3): 398-402 (1970).

Davies, P.F., et al., "Endothelial cell adhesion in real time" *J. Clin. Invest.* 91: 2640-2652 (1993).

Davies, P.F., et al., "Quanitative studies of endothelial cell adhesion" *J. Clin. Invest.* 93: 2031-2038 (1994).

Den Braber, et al., "Effects of parallel surface microgrooves and surface energy on cell growth" *Journal of Biomedical Materials Research* 29: 511-518 (1995).

Fischer, K., et al., "Microstructure gradients in PVD-TiN coatings" *Materials Science Forum* 273-275: 567-572 (1998).

Giancotti, F.G. et al. "Review integrin signaling" *Science*, 285(5430): 1028-1033 (1999).

Glocker, D.A., "Principles and applications of hollow cathode magnetron sputtering sources" *Society of Vacuum Coaters, 38th Annual Technical Conference Proceedings* pp. 298-302 (1995).

Hehrlein, C., et al., "Therapy and prevention: Influence of surface texture and charge on the biocompatibility of endovascular stents"

(56) References Cited

OTHER PUBLICATIONS

University of Heidelberg, Germany; Dept. of Cardiology, Anatomy, and Physical Chemistry, pp. 581-585 (1995).

Holleck, H., et al., "Multilayer PVD coatings for wear protection" *Surface and Coatings Technology* 76-77(1): 328-336 (1997) Abstract Only.

Hoshi, Y., et al., "Thin film coating techniques on wires and inner walls of small tubes via cylindrical magnetron sputtering" *Electrical Engineering in Japan* 103(1): 73-80 (1983).

Kasemo, B., "Biomaterial and implant surfaces: On the role of cleanliness, contamination, and preparation procedures" *J Biomed. Mater Res.: Applied Biomaterials* 22(A2): 145-158 (1988).

Kasemo, B., "Biological surface science" *Surface Science* 500: 656-677 (2002).

Kazmierska, K. et al., "Bioactive coatings for minimally invasive medical devices: Surface modification in the service of medicine" *Recent Patents on Biomedical Engineering* 2: 1-14 (2009).

Lita, A., et al., "Characterization of surface structure in sputtered Al films: Correlation to microstructure evolution" Journal of Applied Sciences 85(2): 876-882 (1999).

Liu, X., et al., "Surface modification of titanium, titanium alloys, and related materials for biomedical applications" *Materials Science and Engineering* R 47: 49-121 (2004).

Loh, I., "Plasma surface modification in biomedical applications" *AST Technical Journal* pp. 1-6 (undated).

Matsuda, T., "Control of cell adhesion, migration and orientation on photochemically microprocessed surfaces" *Journal of Biomedical Materials Research* 32: 165-173.

Palmaz, J, et al. "New advances in endovascular technology" *Texas Heart Institute Journal* 24(3): 156-159 (1997).

Palmaz, J., et al. "Influence of stent design and material composition on procedure outcome" *Journal of Vascular Surgery* 36(5): 1031-1039 (2002).

Sprague, E., et al., "Electrostatic forces on the surface metals as measured by atomic force microscopy" *J. Long Term Eff Med Implants* 10(1-2): 111-125 (2000).

Thronton, John A., "High rate thick film growth" *Ann. Rev. Mater. Sci.* 7: 239-260 (1977).

Thornton, John A., "Influence of apparatus geometry and deposition conditions on the structure and topography of thick sputtered coatings" *J. Vac. Sci. Technol.* 11(4): 666-670 (1974).

Thornton, John A., "The influence of bias sputter parameters on thick copper coatings deposited using a hollow cathode" *Thin Solid Films* 40: 335-344 (1977).

Thornton, John A., "Magnetron sputtering: basic physics and application to cylindrical magnetrons" *J. Vac. Sci. Technol.* 15(2): 171-177 (1978).

Thornton, John A., "Tubular hollow cathode sputtering onto substrates of complex shape" *J. Vac. Sci. Technol.* 12(1): 93-97 (1975).

van der Giessen, WJ. et al., "Marked inflammatory sequelae to implantation of biodegradable and non-biodegradable polymers in porcine coronary arteries" *Circulation* 94(7):1690-1697 (1996).

Wells, David L., "Nonplanar microfabrication" The University of Utah pp: 1-127 (1993).

Zarbakhsh, A., "Characterization of photon-controlled titanium oxide surfaces" *ISIS Experimental Report, Rutherford Appelton Laboratory*, (May 16, 2000); www.isis.rl.ac.uk/isis2001/reports/11144.pdf.

\* cited by examiner

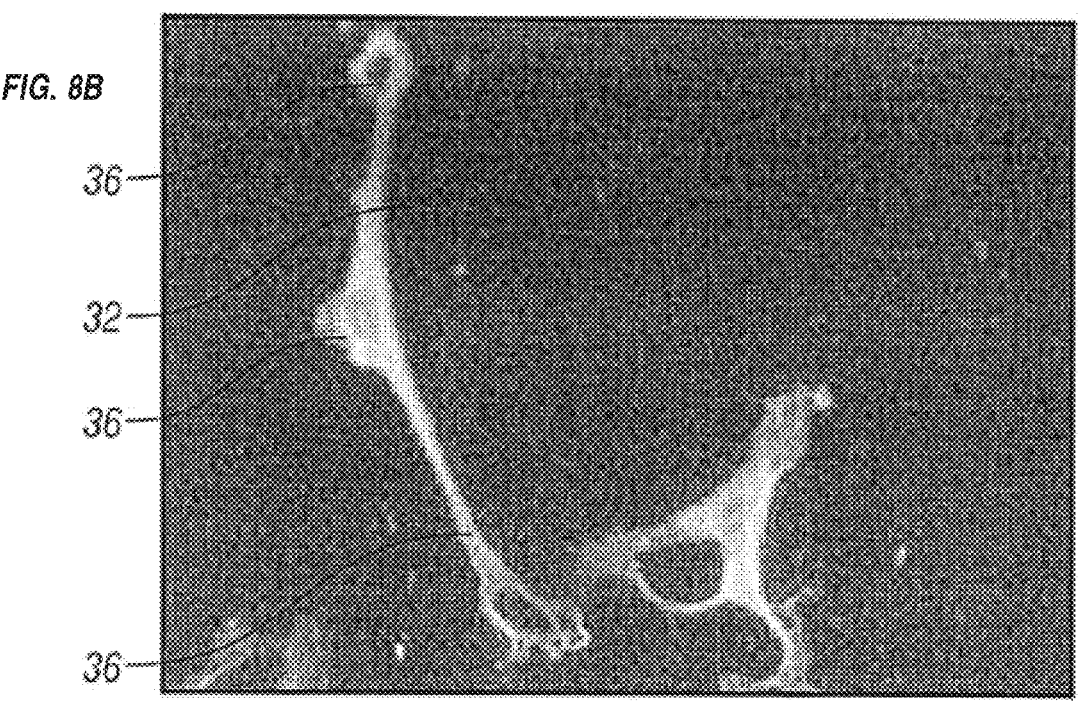
FIG. 8B
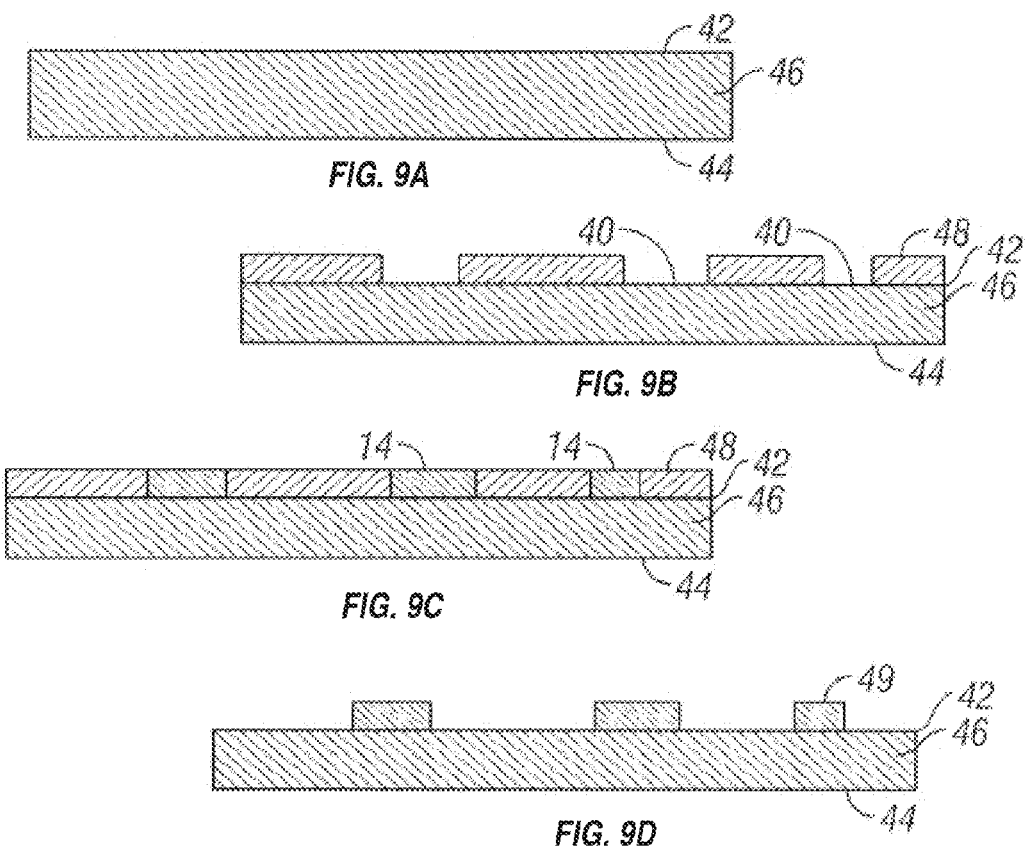
FIG. 9A
FIG. 9B
FIG. 9C
FIG. 9D

IMPLANTABLE MATERIALS HAVING ENGINEERED SURFACES AND METHOD OF MAKING SAME

CROSS-REFERENCE TO RELATED APPLICATIONS

This application is a divisional of U.S. patent application Ser. No. 13/107,510, filed May 13, 2011, which is a continuation-in-part of U.S. patent application Ser. No. 12/428,981, filed Apr. 23, 2009, now U.S. Pat. No. 8,268,340, and is a continuation-in-part of U.S. patent application Ser. No. 11/091,669, filed on Mar. 28, 2005, now U.S. Pat. No. 8,147,859; and claims the benefit of priority to PCT International Patent Application No. PCT/US2003/30383, which bears an international filing date of Sep. 26, 2003; which claims priority to U.S. Provisional Patent Application Ser. No. 60/414,031, filed Sep. 26, 2002, all herein incorporated by reference in their entireties.

BACKGROUND OF THE INVENTION

The present invention relates generally to implantable medical devices and more particularly to controlling surface properties of implantable biocompatible materials suitable for fabrication of implantable medical devices.

Implantable medical devices are fabricated of materials that are sub-optimal in terms of the biological response they elicit in vivo. Many conventional materials used to fabricate implantable devices, such as titanium, polytetrafluoroethylene, silicone, carbon fiber and polyester, are used because of their strength and physiologically inert characteristics. However, tissue integration onto these materials is typically slow and inadequate. Certain materials, such as silicone and polyester, elicit a significant inflammatory, foreign body response that drives fibrous encapsulation of the synthetic material. The fibrous encapsulation may have significant adverse effects on the implant. Moreover, conventional biomaterials have proved inadequate in eliciting a sufficient healing response necessary for complete device integration into the body. For example, in devices that contact blood, such as stents and vascular grafts, attempts to modify such devices to promote endothelial cell adhesion may have a concomitant effect of making the devices more thrombogenic.

When implanted, conventional blood-contacting implantable devices, such as stents, stent-grafts, grafts, valves, shunts and patches, fail to develop a complete endothelial layer, thereby exposing the device material to thrombus formation or smooth muscle cell proliferation, and ultimate failure of the implanted device. It has been recognized that, when implanted into the body, metals are generally considered to have superior biocompatibility than polymers used to fabricate commercially available polymeric grafts.

In cellular interactions with prosthetic material surfaces, cell adhesion to the material surface is mediated by integrins present on cell membranes that interact with the prosthetic surface. Integrins are the most prominent member of a class of extracellular matrix (ECM) adhesion receptors. Integrins are a large family of heterodimeric transmembrane proteins with different α and β subunits. Integrins are regulated at several levels. Modulation of the affinity of the adhesion receptor for ligand, termed affinity modulation, is a mechanism for activation of platelet aggregation and is believed to underlie activation of leukocyte adhesion. Adhesive strengthening by clustering of adhesion receptors or by cytoskeletal-dependent processes such as cell spreading has been shown to be crucial for strong cellular attachment, control of cell growth and cell motility. Under high shear forces present in flowing blood, leukocytes first tether, then roll along the vessel surface. When a local signal, e.g., a cytokine, is released in their vicinity, the leukocyte arrests, develops a firm adhesion then migrates across the endothelium. Tethering, rolling, arrest and adhesion tightening are all known to result from activation of leukocyte integrins.

Once adhered to a surface, cell spreading and migration are associated with assembly of focal adhesion junctions. Cell migration entails the coordination of cytoskeletal-mediated process extension, i.e., filopodia and lamellopodia, formation of adhesive contacts at the leading edge of a cell, breaking adhesive contacts, and cytoskeletal retraction at the trailing edge of the cell. Focal adhesions are comprised of integrins as the major adhesion receptors along with associated cytoplasmic plaque proteins. Assembly of focal adhesions is regulated by extracellular ligand binding events and by intracellular signaling events. Ligand binding controls localization of $\beta 1$- and $\beta 3$-containing integrins into focal adhesions. The cytoplasmic domains of the $\beta$ subunits have intrinsic signals for focal adhesion localization, but incorporation of the integrins into focal adhesions is prevented by the $\alpha$ subunits of the heterodimers. Ligand binding, however, relieves this inhibition and allows the subunit cytoplasmic tail signals to recruit the integrin dimmer into the focal adhesion.

Attempts at coating implanted metal devices, such as stents, with proteins that contain the Arg-Gly-Asp (RGD) attachment site have been made with some success. The RGD sequence is the cell attachment site of a large number of adhesive extracellular matrix, blood, and cell surface proteins and many of the known integrins recognize the RGD sequence in their adhesion protein ligands. Integrin-binding activity may also be reproduced by synthetic peptides containing the RGD sequence. However, bare metal implanted materials will not, of course, have native RGD attachment sites. Thus, metal implantable devices, such as stents, have been derivitized with polymers having RGD attachment sites bound to the polymer matrix.

When prosthetic materials are implanted, integrin receptors on cell surfaces interact with the prosthetic surface. When cells come into contact with the extracellular matrix, such as a prosthetic surface, their usual response is to extend filopodia, and integrins at the tip of the filopodia bind to the extracellular matrix and initiate the formation of focal adhesions. Actin-rich lamellipodia are generated, often between filopodia, as the cell spreads on the extracellular matrix. Fully developed focal adhesions and associated actin stress fibers ensue. These same evens occur during cell migration as cells extend lamellipodia and form focal adhesions to derive the traction necessary for movement. Giancotti, F. G., et al. *Science*, 285:13 August 1999, 1028-1032.

The integrin receptors are specific for certain ligands in vivo. If a specific protein is adsorbed on a prosthetic surface and the ligand exposed, cellular binding to the prosthetic surface may occur by integrin-ligand docking. It has also been observed that proteins bind to metals in a more permanent fashion than they do to polymers, thereby providing a more stable adhesive surface. The conformation of proteins coupled to surfaces of most medical metals and alloys appears to expose greater numbers of ligands and attract endothelial cells having surface integrin clusters to the metal or alloy surface, preferentially over leukocytes.

Because of their greater adhesive surface profiles, metals are also susceptible to short-term platelet activity and/or thrombogenicity. These deleterious properties may be offset by administration of pharmacologically active antithrombogenic agents in routine use today. Surface thrombogenicity usually disappears 1-3 weeks after initial exposure. Antithrombotic coverage is routinely provided during this period of time for coronary stenting. In non-vascular applications such as musculoskeletal and dental, metals have also greater tissue compatibility than polymers because of similar molecular considerations. The best article to demonstrate the fact that all polymers are inferior to metals is van der Giessen, W J. et al. *Marked inflammatory sequelae to implantation of biodegradable and non-biodegradable polymers in porcine coronary arteries*, Circulation, 1996:94(7):1690-7.

Normally, endothelial cells (EC) migrate and proliferate to cover denuded areas until confluence is achieved. Migration, quantitatively more important than proliferation, proceeds under normal blood flow roughly at a rate of 25 µm/hr or about 2.5 times the diameter of an EC, which is nominally 10 µm. EC migrate by a rolling motion of the cell membrane, coordinated by a complex system of intracellular filaments attached to clusters of cell membrane integrin receptors, specifically focal contact points. The integrins within the focal contact sites are expressed according to complex signaling mechanisms and eventually couple to specific amino acid sequences in substrate adhesion molecules. An EC has roughly 16-22% of its cell surface represented by integrin clusters. Davies, P. F., Robotewskyi A., Griem M. L. *Endothelial cell adhesion in real time*. J. Clin. Invest. 1993; 91:2640-2652, Davies, P. F., Robotewski, A., Griem, M. L., *Qualitiative studies of endothelial cell adhesion*, J. Clin. Invest. 1994; 93:2031-2038. This is a dynamic process, which involves more than 50% remodeling in 30 minutes. The focal adhesion contacts vary in size and distribution, but 80% of them measure less than 6 µm², with the majority of them being about 1 µm², and tend to elongate in the direction of flow and concentrate at leading edges of the cell. Although the process of recognition and signaling to determine specific attachment receptor response to attachment sites is not completely understood, availability of attachment sites will favorably influence attachment and migration. Materials commonly used as medical grafts, such as polymers, do not become covered with EC and therefore do not heal after they are placed in the arteries.

There have been numerous attempts to increase endothelialization of implanted medical devices such as stents, including covering the stent with a polymeric material (U.S. Pat. No. 5,897,911), imparting a diamond-like carbon coating onto the stent (U.S. Pat. No. 5,725,573), covalently binding hydrophobic moieties to a heparin molecule (U.S. Pat. No. 5,955,588), coating a stent with a layer of blue to black zirconium oxide or zirconium nitride (U.S. Pat. No. 5,649, 951), coating a stent with a layer of turbostratic carbon (U.S. Pat. No. 5,387,247), coating the tissue-contacting surface of a stent with a thin layer of a Group VB metal (U.S. Pat. No. 5,607,463), imparting a porous coating of titanium or of a titanium alloy, such as Ti—Nb—Zr alloy, onto the surface of a stent (U.S. Pat. No. 5,690,670), coating the stent, under ultrasonic conditions, with a synthetic or biological, active or inactive agent, such as heparin, endothelium derived growth factor, vascular growth factors, silicone, polyurethane, or polytetrafluoroethylene (U.S. Pat. No. 5,891,507), coating a stent with a silane compound with vinyl functionality, then forming a graft polymer by polymerization with the vinyl groups of the silane compound (U.S. Pat. No. 5,782,908), grafting monomers, oligomers or polymers onto the surface of a stent using infrared radiation, microwave radiation or high voltage polymerization to impart the property of the monomer, oligomer or polymer to the stent (U.S. Pat. No. 5,932,299). However, all these approaches do not address the lack of endothelialization of polymer grafts.

Overall rate to reach confluence for the endothelial cells on the blood contact surface of implanted medical device is mainly determined by two factors, the rate of cell movement and rate of cell proliferation, with the first being more important. The rate of cell movement further comprises three interrelated steps. Initially, a cell forms lamellipodia and filopodia that protrude outward. This step involves reassembly of actins in the forefront of lambaepolia. After protrusion of lamellipodia from one or multiple points from the cell membrane, the front end of the lamellipodia will form a close attachment, called focal adhesion point, to the substratum through the interaction of integrin on the cell membrane and extracellular matrix binding site. The final step of cell movement involves the contraction of the posterior end through the action of myosin II. The formation of a focal adhesion point is critical for the cell movement because the protruding lamellipodia will otherwise fold back. Without the tension force from the focal adhesion point, a cell loses the contraction from the posterior end and hence stops moving.

Availability of attachment sites on the substratum is not only important for the focal adhesion point formation, but also important for propagation. It has been shown that cells are forced to spread, survive better and proliferate faster than cells that are confined to the same amount of surface area (*Science* 276:1425-1428, 1997). This may explain why spreading of neighbor cells stimulate a cell to proliferate, after cells are lost from epithelium.

The formation of extracellular matrix (ECM) is, to much extent, determined by the cells within it because molecules which form ECM are secreted by the cells. Subsequently, the structure of the ECM, and hence the distribution of attachment sites on the ECM for the integrin binding, determines the focal adhesion point formation, the critical step in cell movement. Therefore, proper distribution of integrin binding sites on the surface of an implanted medical device substantially determines the speed of reendothelialization from the ends surrounding the device.

There still remains a need for a medical device that stimulates endothelial proliferation and movement when implanted in order to form an endothelial layer over the medical device. Furthermore, there is a remaining need for a method of fabricating such a medical device.

SUMMARY OF THE INVENTION

In one embodiment, an implantable biocompatible material includes one or more vacuum deposited layers of biocompatible materials deposited upon a biocompatible base material. At least a top most vacuum deposited layer includes a homogeneous molecular pattern of distribution along the surface thereof and comprises a patterned array of geometric physiologically functional features.

In another embodiment, an implantable biocompatible material includes a plurality of layers of biocompatible materials formed upon one another into a self-supporting multi-layer structure. The plurality of layers includes a vacuum deposited surface layer having a homogeneous molecular pattern of distribution along the surface thereof and comprises a patterned array of geometric physiologically functional features.

In a further embodiment, a method for making an implantable biocompatible material is presented. The method includes the steps of providing an implantable biocompatible material having at least one surface intended to contact tissue of body fluids in vivo and providing a mask having a defined pattern of openings corresponding in size and spacing to a predetermined distribution of binding domains to be imparted to the at least one surface.

The method further includes the steps of treating the at least one surface of the biocompatible material through the mask by at least one of three techniques. The first technique includes vacuum depositing a layer of material onto the at least one surface, wherein the vacuum deposited layer is different from the at least one surface immediately therebeneath in a material property selected from the group of material properties consisting of: grain size, grain phase, grain material composition, surface topography, and transition temperature, and removing the mask to yield a plurality of binding domains defined on the at least one surface of the implantable, biocompatible material. The second technique includes vacuum depositing a layer of sacrificial material onto the at least one surface, removing the mask from the at least one surface, vacuum depositing a second layer of material onto the at least one surface, wherein the second vacuum deposited layer is different from the at least one surface immediately therebeneath in a material property selected from the group of material properties consisting of: grain size, grain phase, grain material composition, surface topography, and transition temperature, and removing the sacrificial material to yield a plurality of binding domains defined on the at least one surface of the implantable, biocompatible material. The third technique includes photo irradiating the at least one surface to photochemically alter the at least one surface, and removing the mask to yield a plurality of binding domains defined on the at least one surface of the implantable, biocompatible material.

BRIEF DESCRIPTION OF THE FIGURES

FIGS. 8A-8B are photomicrographs showing the formation of multiple focal adhesion points of a migrating cell and its attachment to the inventive geometric physiologically functional features.

FIGS. 9A-9D are cross-sectional diagrammatic views of one embodiment, the combination of a-d representing the steps to make an inventive implantable material with elevated geometric physiologically functional features.

The foregoing and other features and advantages of the disclosure are apparent from the following detailed description of exemplary embodiments, read in conjunction with the accompanying drawings; wherein like structural or functional elements are designated by like reference numerals.

DETAILED DESCRIPTION OF THE PREFERRED EMBODIMENTS

Figure 1:
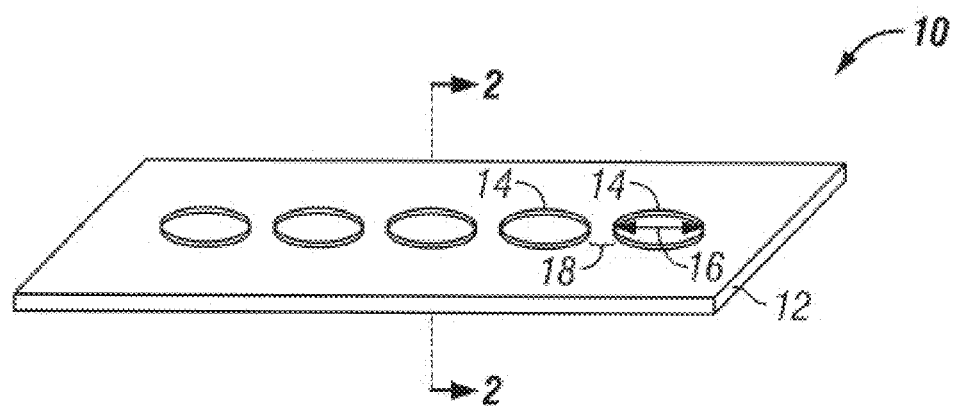
FIG. 1 is a perspective view of one embodiment including evenly distributed elevated geometric physiologically functional features on the surface of an implantable material.

In accordance with one embodiment, the capacity for complete endothelialization of conventional implantable materials, including metals and polymers, may be enhanced by imparting a pattern of chemically and/or physiochemically active geometric physiologically functional features onto a blood contacting surface of the implantable material. The inventive implantable metal devices may be fabricated of polymers, pre-existing conventional wrought metallic materials, such as stainless steel or nitinol hypotubes, or may be fabricated by thin film vacuum deposition techniques. In accordance with one embodiment, it is preferable to fabricate the inventive implantable materials and resulting devices by vacuum deposition of either or both of the base implant material and the chemically and/or physiochemically active geometric physiologically functional features. Vacuum deposition permits greater control over many material characteristics and properties of the resulting material and formed device. For example, vacuum deposition permits control over grain size, grain phase, grain material composition, bulk material composition, surface topography, mechanical properties, such as transition temperatures in the case of a shape memory alloy. Moreover, vacuum deposition processes will permit creation of devices with greater material purity without the introduction of large quantities of contaminants that adversely affect the material and, therefore, the mechanical and/or biological properties of the implanted device. Vacuum deposition techniques also lend themselves to fabrication of more complex devices than those that are manufactured by conventional cold-working techniques. For example, multi-layer structures, complex geometrical configurations, extremely fine control over material tolerances, such as thickness or surface uniformity, are all advantages of vacuum deposition processing. The embodiments disclosed herein to may replace polymer grafts with metal grafts that can potentially become covered with EC and can heal completely. Furthermore, heterogeneities of materials in contact with blood flow are preferably controlled by using vacuum deposited materials.

In vacuum deposition technologies, materials are formed directly in the desired geometry, e.g., planar, tubular, etc. The common principle of vacuum deposition processes is to take a material in a minimally processed form, such as pellets or thick foils, known as the source material and atomize them. Atomization may be carried out using heat, as is the case in physical vapor deposition, or using the effect of collisional processes, as in the case of sputter deposition, for example. In some forms of deposition a process such as laser ablation, which creates microparticles that typically consist of one or more atoms, may replace atomization; the number of atoms per particle may be in the thousands or more. The atoms or particles of the source material are then deposited on a substrate or mandrel to directly form the desired object. In other deposition methodologies, chemical reactions between ambient gas introduced into the vacuum chamber, i.e., the gas source, and the deposited atoms and/or particles are part of the deposition process. The deposited material includes compound species that are formed due to the reaction of the solid source and the gas source, such as in the case of chemical vapor deposition. In most cases, the deposited material is then either partially or completely removed from the substrate, to form the desired product.

A first advantage of vacuum deposition processing is that vacuum deposition of the metallic and/or pseudometallic films permits tight process control and films may be deposited that have a regular, homogeneous atomic and molecular pattern of distribution along their fluid-contacting surfaces. This avoids the marked variations in surface composition, creating predictable oxidation and organic adsorption patterns and has predictable interactions with water, electrolytes, proteins and cells. In particular, EC migration is supported by a homogeneous distribution of binding domains that serve as natural or implanted cell attachment sites in order to promote unimpeded migration and attachment.

Secondly, in addition to materials and devices that are made of a single metal or metal alloy layer, the inventive grafts may be comprised of a layer of biocompatible material or of a plurality of layers of biocompatible materials formed upon one another into a self-supporting multilayer structure because multilayer structures increase the mechanical strength of sheet materials, or to provide special qualities by including layers that have special properties such as superelasticity, shape memory, radio-opacity, corrosion resistance etc. Vacuum deposition technologies may deposit layered materials and thus films possessing exceptional qualities may be produced. Layered materials, such as superstructures or multilayers, are commonly deposited to take advantage of some chemical, electronic, or optical property of the material as a coating; a common example is an antireflective coating on an optical lens. Multilayers are also used in the field of thin film fabrication to increase the mechanical properties of the thin film, specifically hardness and toughness.

Thirdly, the design possibilities for possible configurations and applications of the inventive graft are greatly realized by employing vacuum deposition technologies. Specifically, vacuum deposition is an additive technique that lends itself toward fabrication of substantially uniformly thin materials with potentially complex three dimensional geometries and structures that cannot be cost-effectively achieved, or in some cases achieved at all, by employing conventional wrought fabrication techniques. Conventional wrought metal fabrication techniques may entail smelting, hot working, cold working, heat treatment, high temperature annealing, precipitation annealing, grinding, ablation, wet etching, dry etching, cutting and welding. All of these processing steps have disadvantages including contamination, material property degradation, ultimate achievable configurations, dimensions and tolerances, biocompatibility and cost. For example conventional wrought processes are not suitable for fabricating tubes having diameters greater than about 20 mm, nor are such processes suitable for fabricating materials having wall thicknesses down to about 1 µm with sub-µm tolerances.

The embodiments disclosed herein takes advantage of the discovered relationship between chemically or physiochemically-active geometric physiologically functional features defined and distributed on a blood contact surface and enhanced endothelial cell binding, proliferation and migration over the blood contact surface of the implantable material. The embodiments disclosed herein involve focal adhesion point formation during cellular movement and the anchorage dependence, that spreading cells proliferate faster than non-spreading cells. The addition of a patterned array of geometric physiologically functional features, which have a hydrophobic, hydrophilic or surface energy difference relative to the surface onto which the geometric physiologically functional features are added, enhances the binding, proliferation and migration of endothelial cells to and between the geometric physiologically functional features and across the surface.

The geometric physiologically functional features disclosed herein may be formed on, in, or through one or more layers of vacuum deposited biocompatible material. In a first embodiment, the one or more layers of vacuum deposited biocompatible material are deposited on a layer of bulk material. In a second embodiment, a plurality of layers of vacuum deposited biocompatible material is deposited on one another to form a self-supporting multilayer structure. Each of the first and second embodiments includes several aspects. In a first aspect, the geometric physiologically functional features may have a non-zero thickness corresponding to a thickness of one or more layers of the vacuum deposited material. Alternatively, in other aspects, the geometric physiologically functional features may have a zero thickness or a thickness greater than one or more layers of the vacuum deposited material.

Below about 3 µm in thickness, the interactions between endothelial cells and the geometric physiologically functional features are primarily chemical and electrochemical. Geometric physiologically functional features having thicknesses greater than 3 µm and up to about 20 µm may also be employed in the embodiments disclosed herein, it being understood that as the thickness of the geometric physiologically functional feature increases there is a decreasing chemical and/or electrochemical interaction between the geometric physiologically functional feature and the endothelial cells and an increasing physical interaction (topographic guidance effect).

Additionally, UV irradiation may be employed to oxidize titanium or titanium-alloy surfaces, photochemical alteration of the surface titanium oxides alter the hydrophobicity of the exposed titanium oxides and act as affinity binding and migration sites for endothelial cell attachment and proliferation across a titanium or titanium-alloy surface. Where UV irradiation is employed, the thickness of the photochemically altered regions of titanium oxide are, for all practical purposes, 0 μm. Thus, within the context of the present application, the term "geometric physiologically functional features" is intended to include both physical members and photochemically-altered regions having thicknesses having thicknesses down to 0 μm.

In FIG. 1, a portion of an implantable material 10 showing the surface material 12 with described elevated geometric physiologically functional features 14 is illustrated. The geometric physiologically functional features are elevated from the surface of the implantable material to a height ranging from about 1 nm to about 20 μm. Preferably, the height of the geometric physiologically functional feature 14 ranges from about 1 nm to about 3 μm. The shape of geometric physiologically functional features can be either circular, square, rectangle, triangle, parallel lines, straight or curvilinear lines or any combination thereof. Each of the geometric physiologically functional features is preferably from about 1 nm to about 75 μm, and preferably from about 1 nm to 50 μm in feature width 16, or feature diameter if the geometric physiologically functional feature is circular. A gap distance 18 between each of the geometric physiologically functional features may be less than, about equal to or greater than the feature width 16, i.e., between about 1 nm to about 75 μm edge-to-edge.

Figure 2:
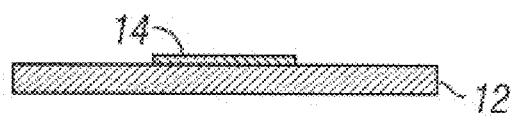
FIG. 2 is cross-sectional view of FIG. 1 along line 2-2.

FIG. 2 is a cross-sectional view along line 2-2 in FIG. 1. One of the elevated geometric physiologically functional features 14 is shown on the surface 12 of the implantable material.

Figure 3:
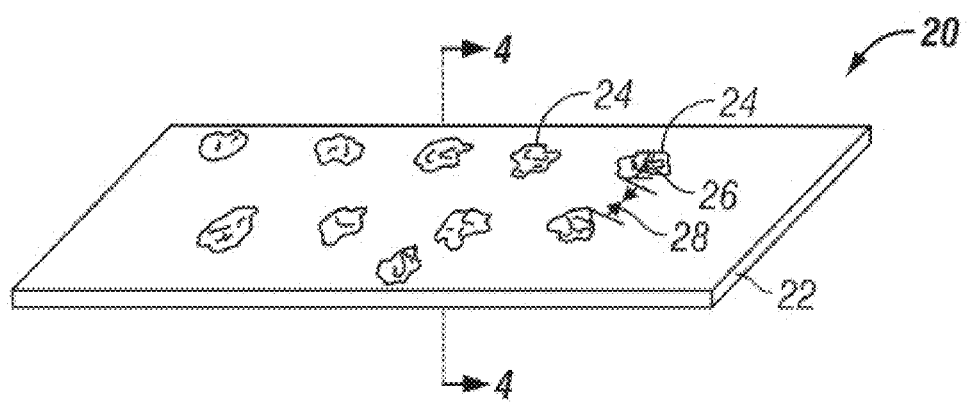
FIG. 3 is a perspective view of one embodiment including evenly distributed chemically defined geometric physiologically functional features on the surface of an implantable material.

In FIG. 3, a layer of a titanium or titanium-alloy material 20 is heating to oxidize and form titanium dioxide on the surface of the material 20. In one embodiment, the layer of titanium or titanium-alloy material 20 is deposited over one or more layers of vacuum deposited material in a self-supporting multilayer structure. In another embodiment, the layer of titanium or titanium-alloy material 20 is deposited over a bulk material that may have one or more layers of vacuum deposited material deposited thereon.

The geometric physiologically functional features 24 are formed by exposing the layer of material 20 to UV through a pattern mask. UV irradiation alters the titanium oxides in the areas of geometric physiologically functional features 24, thereby chemically altering the geometric physiologically functional features 24 relative to the surrounding the surrounding surface area 22 of material layer of material 20. The shape of geometric physiologically functional features can be circular, square, rectangle, triangle, parallel lines, intersecting lines or any combination. Each of the geometric physiologically functional features is from about 1 nanometer to about 75 μm, and preferably from about 1 nanometer to about 50 μm in feature width 16, or feature diameter if the geometric physiologically functional feature is circular. The gap distance 28 between each component of the geometric physiologically functional features may be less than, about equal to or greater than the feature width 26.

Figure 4:
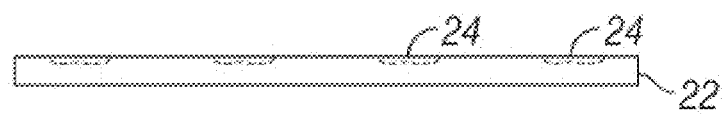
FIG. 4 is a cross-sectional view of FIG. 3 along line 4-4.

FIG. 4 is a cross-sectional view of FIG. 3 along line 4-4. The described geometric physiologically functional features 24 are indicated by the dotted lines, which indicate that the geometric physiologically functional features 24 are at the same level of the surrounding surface 22.

Figure 5:
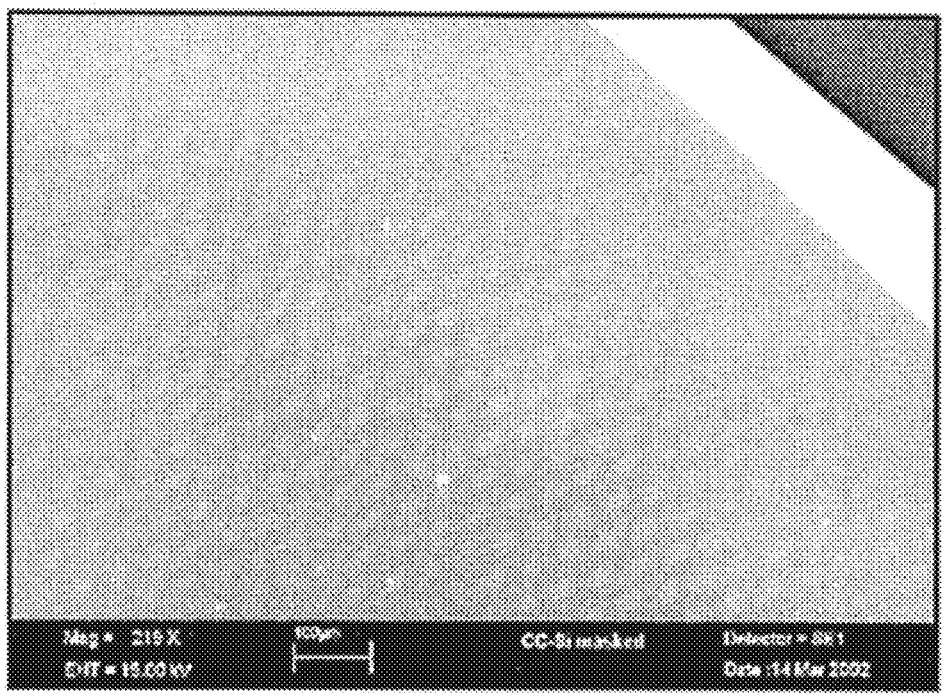
FIG. 5 is a photomicrograph showing one embodiment including geometric physiologically functional features as carbon coated silicon.

FIG. 5 shows geometric physiologically functional features that are evenly distributed across the at least one surface of the implantable material that contacts body fluid, preferably blood. As disclosed in FIG. 1 and FIG. 2, the geometric physiologically functional features are elevated from the rest of the surface to a height ranging from about 1 nanometer to about 20 micrometers. Preferably, the height of the geometric physiologically functional feature ranges from about 1 nanometer to about 3 micrometers. The shape of the geometric physiologically functional features is not confined within the shape that is shown. The shape of the chemically defined domain can also be any of circle, square, rectangle, and triangle, parallel lines, intersecting lines or any combination of the above.

Figure 6A:
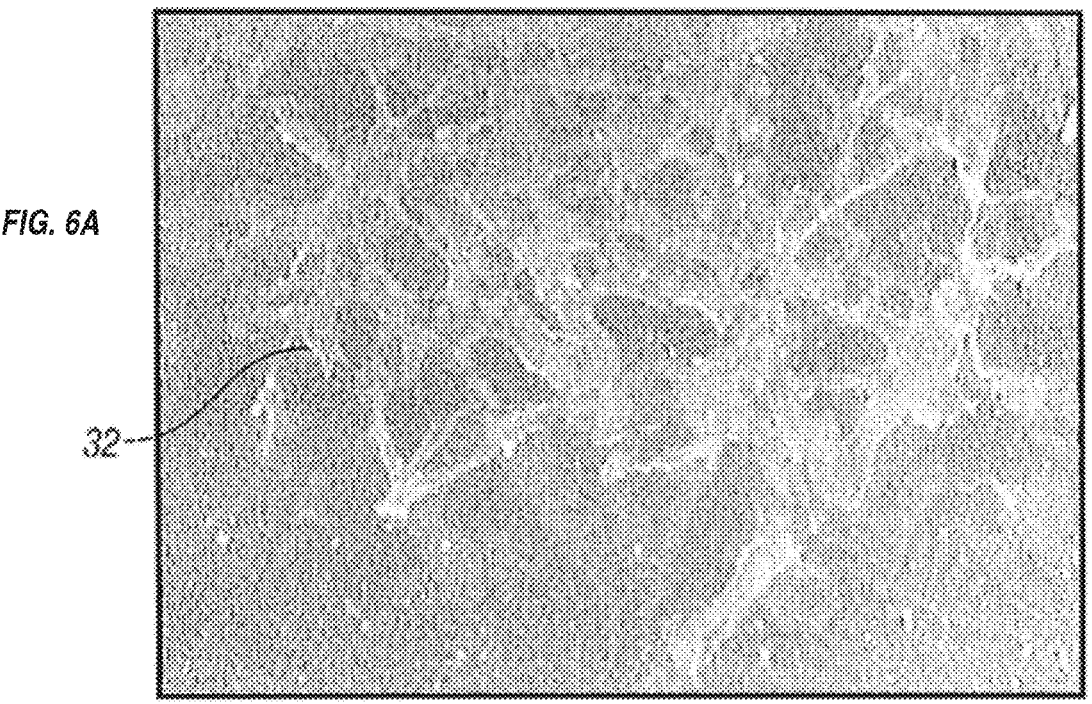
FIGS. 6A-6C are photomicrographs showing cellular migration on the surface with no inventive geometric physiologically functional features versus on the surface with inventive geometric physiologically functional features.
Figure 6B:
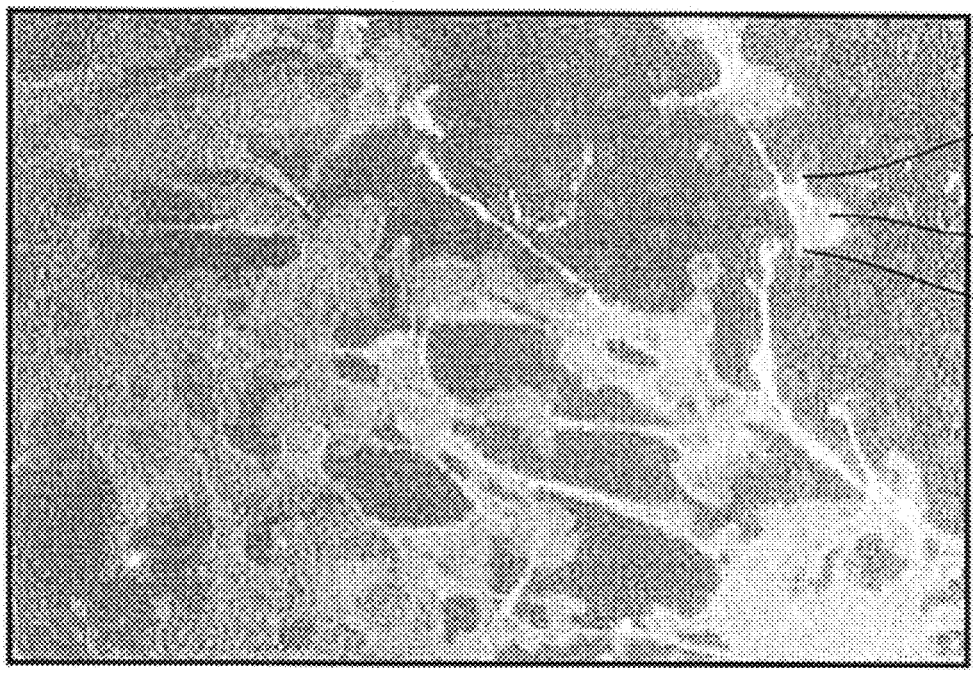

FIG. 6A shows the cell 32 spreading on the surface of hydrophilic treated Si. FIG. 6B shows the cell 32 spreading on the surface of hydrophilic treated Si with circular dots that are 15 microns in diameter. Cells in FIG. 6B appear to have much more focal adhesion points 36 than those in FIG. 6A. Because these geometric physiologically functional features provide for cell attachment, acting as affinity domains, the size of each of these affinity domains relative to the size of an endothelial cell determines the availability of affinity domains to the subsequent round of cell movement. According to one embodiment, the preferred size of each of the individual component of the geometric physiologically functional features is about 1 nm to about 75 μm, and preferably from about 1 nm to 50 μm in feature width, or diameter if the geometric physiologically functional feature is circular. Focal adhesion point formation is the critical step in cell movement and cell proliferation; therefore, geometric physiologically functional features such as carbon dots on the hydrophilic Si surface promote cell movement. Spreading of cells promotes cell proliferation, protein synthesis, and other cell metabolic functions. Promoting cell movement and cell proliferation ultimately accelerates covering of the implanted implantable material with endothelial cells on exposed surfaces having the geometric physiologically functional features. Although the geometric physiologically functional features shown in FIG. 6B are circular, the shape of the geometric physiologically functional features are not limited to this particular embodiment.

Figure 6C:
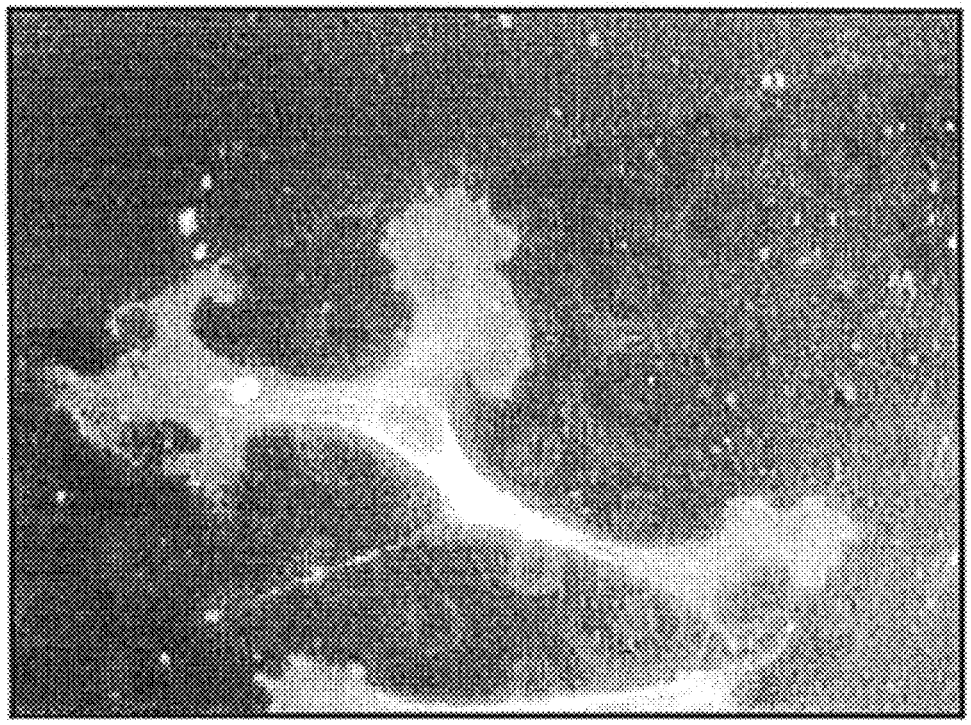

FIG. 6C is a magnification of a portion of the image of FIG. 6B. Multiple focal adhesion points 36 are again shown. Wide spreading of the cell is primarily due to the formation of multiple focal adhesion points on the circular geometric physiologically functional features. Extensive spreading of the cells is beneficial towards endothelialization because it promotes cell movement and cell proliferation.

Figure 7:
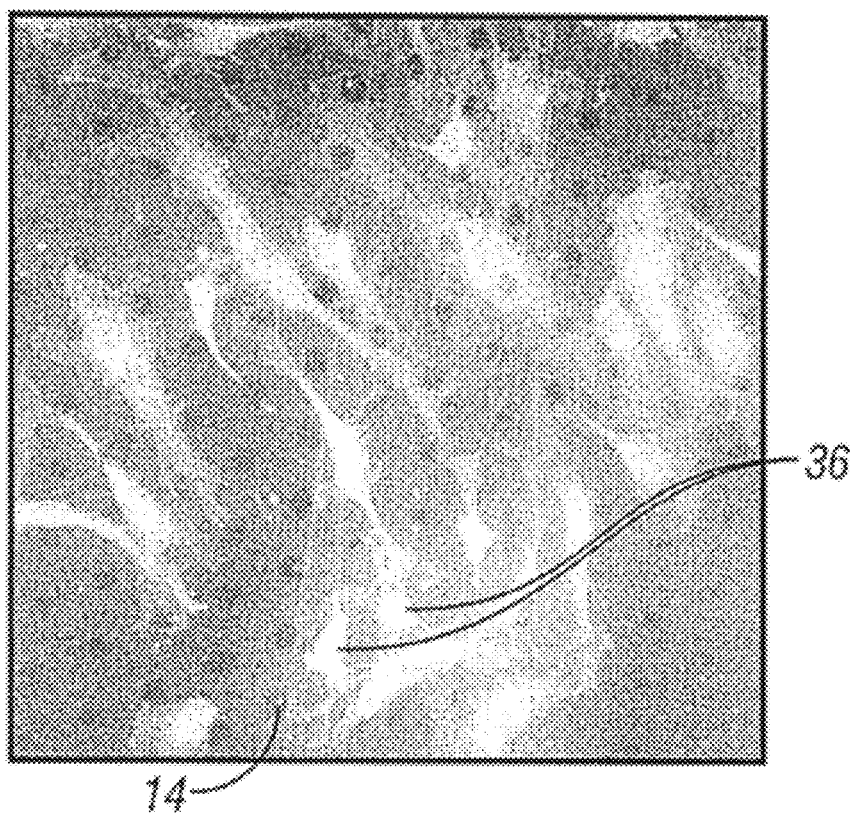
FIG. 7 is a photomicrograph showing the stained focal adhesion points close to the geometric physiologically functional features.

FIG. 7 shows the stained focal adhesion points 36 of human aotic endothelial cells (HAEC) on the surface of an implantable material with geometric physiologically functional features 14 that are in the form of carbon dots. The focal adhesion points are located at or very close to the geometric physiologically functional features 14. These focal adhesion points serve as tension points for the cell to contract from the opposite end of the cell and hence promote cell movement.

Figure 8A:
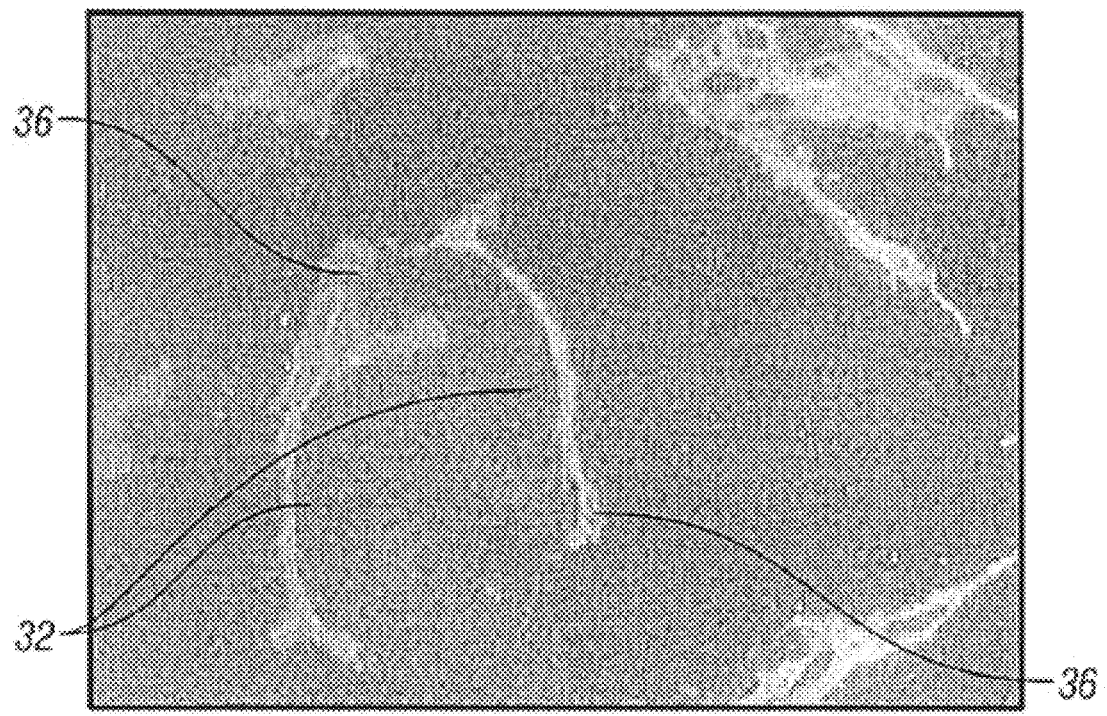

FIG. 8A shows the wide spreading of cells 32 and focal multiple focal adhesion points 36 on the surface of an implantable material with geometric physiologically functional features that are in the form of NiTi dots of 25 micrometers in diameter. The NiTi dots are invisible due to the weak contrast between the NiTi dots and surrounding Si surface.

FIG. 8B shows a magnified slide of a human aortic epithelial cell 32, as shown in FIG. 8A. Multiple focal adhesion points 36 are shown to encapsulate the NiTi dots patterned on the hydrophilic Si surface.

Referring to FIG. 9A, a portion of an implantable material 46 with surface 42 and 44 is shown.

Referring to FIG. 9B, according to one embodiment, a machined mask 48 having laser-cut holes 40 of defined size ranging from about 1 nm to about 75 µm, and preferably from about 1 nm to 50 µm, patterned throughout coats at least one surface 42 of the implantable material 46 and is tightly adhered to the covered surface 42.

Referring to FIG. 9C, a thin film of material 14 was deposited into the space as defined by the holes 40, as seen in FIG. 9B, in the mask 48 by thin film deposition procedures.

Referring to FIG. 9D, after deposition, the mask is removed to reveal the geometric physiologically functional features 49 patterned across the at least one surface 42 of the implantable material 46.

As described above, the shape of the holes in the mask could be in any of the shapes described for the geometric physiologically functional features including: circle, square, rectangle, triangle, parallel lines and intersecting lines, or any combination thereof. In the thin film deposition embodiment of the manufacturing the geometric physiologically functional features, the geometric physiologically functional features are elevated from the surface of the implantable material. The thickness of the geometric physiologically functional features is based upon the thickness of the holes in the mask, the thickness ranging from about 1 nm to about 20 micrometers. Preferably, the thickness of the holes in the mask range from about 1 nm to about 3 micrometers.

Figure 11A:
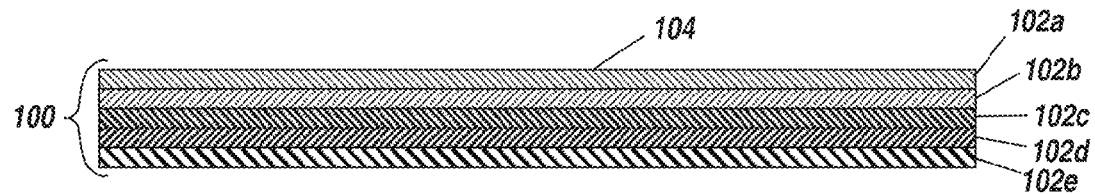
FIG. 11A illustrates a cross-sectional view of layers of vacuum deposited material.
Figure 11B:
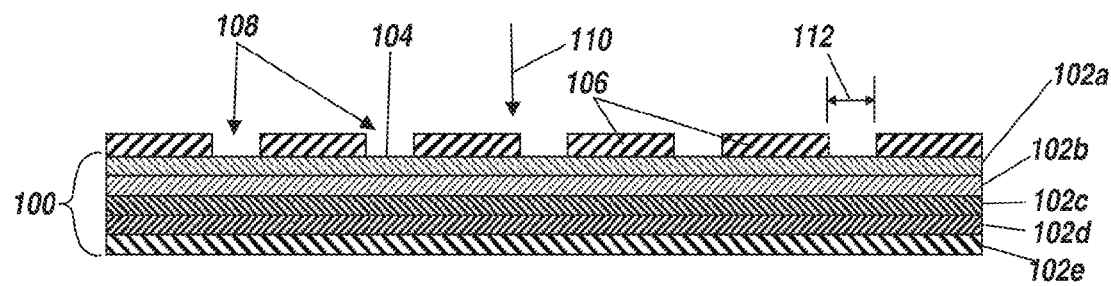
FIG. 11B illustrates a cross-sectional view of a mask disposed over a surface of the layers of vacuum deposited material of FIG. 11A.

The variations of geometric physiologically functional features may be added to a surface of an implantable biocompatible material by vacuum depositing a layer or layers of biocompatible material on the surface. In one embodiment, the geometry of the layer or layers of deposited material defines the geometric physiologically functional features. For example, an implantable material 100 has a surface 104, as illustrated in FIG. 11A. In one embodiment, the implantable biocompatible material may comprise one or more layers 102 of vacuum deposited material formed into a self-supporting structure, as illustrated by FIG. 11A showing a first layer 102a, a second layer 102b, a third layer 102c, a fourth layer 102d, and a fifth layer 102e. In another embodiment, the implantable biocompatible material includes a bulk material, either a bulk material alone or a bulk material covered by the one or more layers 102a-102e of vacuum deposited biocompatible material. Five layers 102a-102e of vacuum deposited material are illustrated; however, any number of layers may be included as desired or appropriate.

The one or more layers 102, may have thicknesses that are the same or different as desired or appropriate. Each layer may have a thickness in a range from about 1 nanometer to about 20 micrometers, from about 1 nanometer to about 10 micrometers, from about 1 nanometer to about 5 micrometers, or from about 1 nanometer to about 3 micrometers. Alternating layers 102 of varying thicknesses may be applied as to accommodate the geometric physiologically functional features.

In this embodiment, the geometric physiologically functional features may be added to the surface 104 by adding one or more layers 102 of vacuum deposited material. For example, referring to FIGS. 11B-11E, in one process, a mask 106 having holes 108 of defined size disposed therethrough and patterned throughout coats and is tightly adhered to at least a first portion of the surface 104. The holes 108 may be cut through the mask 106, for example, by using a laser, wet or dry chemical etching, or other like methods for forming holes through a material, or the mask 106 may be fabricated including the holes 108. The thickness of the holes 108 may range about 1 nanometer to about 20 micrometers, from about 1 nanometer to about 10 micrometers, from about 1 nanometer to about 5 micrometers, or from about 1 nanometer to about 3 micrometers.

Figure 11C:
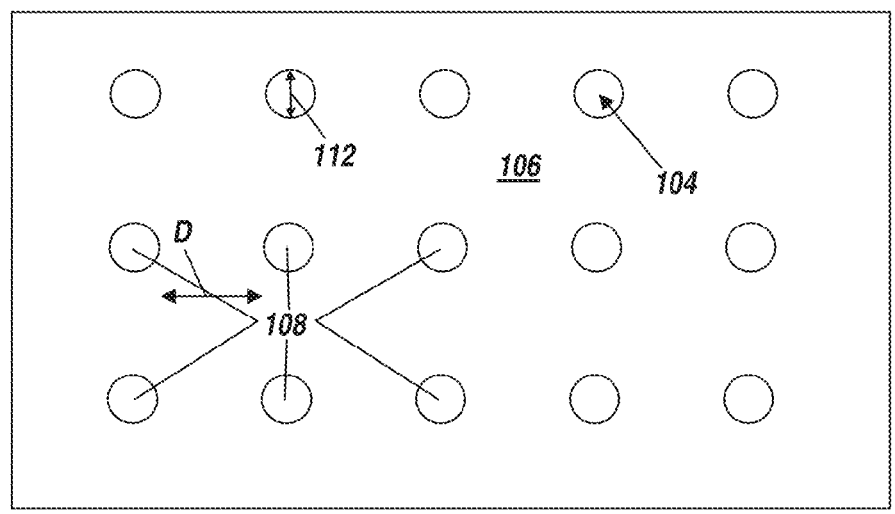
FIG. 11C illustrates a plan view of the mask of FIG. 11B.

The shape of the holes 108 as seen in FIG. 11C or as looking in the direction of arrow 110 may be any of the shapes described for the geometric physiologically functional features including: circle, square, rectangle, triangle, polygonal, hexagonal, octagonal, elliptical, parallel lines and intersecting lines, or any combination thereof. The holes 108 may have a width 112, or diameter 112 if the holes are circular, in a range between about 1 nanometer and about 75 micrometers, between about 1 nanometer and about 50 micrometers, between about 1 nanometer and about 2000 nanometers, or between about 1 nanometer and about 200 nanometers. Adjacent holes 108 may be spaced apart by a distance D in a range from about 1 nanometer to about 20 micrometers, from about 1 nanometer to about 10 micrometers, from about 1 nanometer to about 5 micrometers, or from about 1 nanometer to about 3 micrometers. The distance D may be less than, about equal to or greater than the width 112. In another embodiment (not shown), the width 112 of each of the holes 108 and/or the distance D between adjacent holes 108 may vary in size to form a patterned array of the holes 108.

Figure 11D:
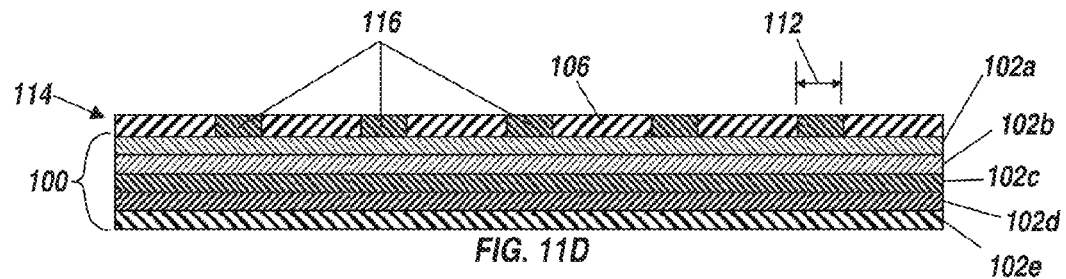
FIG. 11D illustrates a cross-sectional view of material deposited into a space defined by holes of the mask of FIG. 11B.

Referring to FIG. 11D, a layer 114 of material was deposited into a space as defined by the holes 108 in the mask 106 by vacuum deposition. The layer 114 has a thickness essentially the same as that of the mask 106. In some embodiments, the thickness of the mask may be variable across the mask 106. After removal of the mask 106, geometric physiologically functional features 116 are revealed patterned across the surface 104 of the implantable material 100. Each of the geometric physiologically functional features 116 includes a top surface 118. Each of the geometric physiologically functional features 116 has dimensions as described hereinabove for the holes 108 in the mask 106.

In another embodiment where geometry of the layer or layers of deposited material defines the geometric physiologically functional features, a patterned array of recesses may be formed each having a hydrophobic, hydrophilic or surface energy difference relative to the surface into which the recesses are added, meaning a top most surface of the deposited layers, the difference enhancing the binding, proliferation and migration of endothelial cells to and between the recesses and across the surfaces, recessed and top most. The hydrophobic, hydrophilic or surface energy differences relative to the surface may be formed, by way of example, any of the methods disclosed in commonly assigned U.S. patent application Ser. No. 12/428,981, filed Apr. 23, 2009, incorporated by reference herein.

In this embodiment, the recesses may be formed by a relative lack of deposition of a layer or layers onto a surface, or by machining recesses through a layer or layers of material vacuum deposited on a surface. For example, to produce a pattern of recesses similar to the pattern of geometric physiologically functional features 116 illustrated in FIG. 11E, in one example, a process begins by executing the steps described hereinabove with regard to FIGS. 11A-11E, to produce the pattern of geometric physiologically functional features 116 illustrated in FIG. 11E, except in this embodiment, the layer 114 of material is a sacrificial layer of material that is removed in a subsequent step.

Figure 12A:
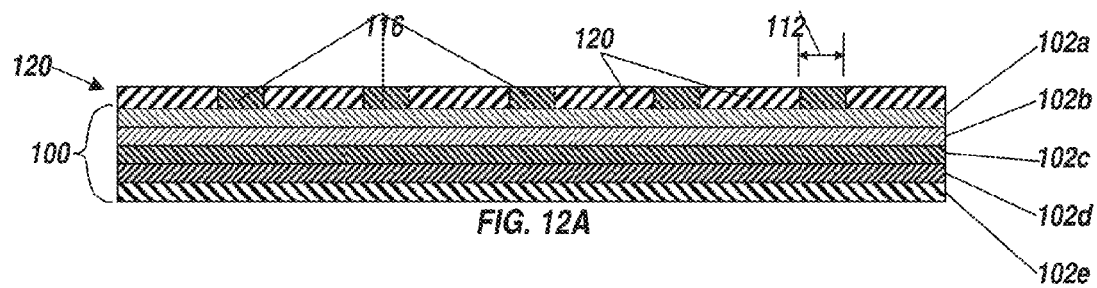
FIG. 12A illustrates a cross-sectional view of vacuum deposition of a layer of material onto a surface of layers of vacuum deposited material and into a space defined by a sacrificial layer of material previously deposited onto the surface.
Figure 12B:
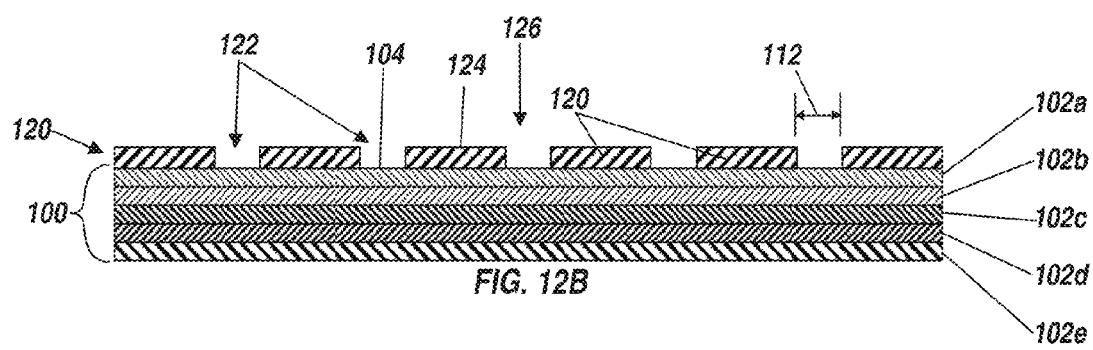
FIGS. 12B-12D illustrate a cross-sectional view of recessed geometric physiologically functional features.

Referring to FIGS. 12A and 12B, a layer 120 of material is deposited into spaces between the geometric physiologically functional features 116 by vacuum deposition. The layer 120 has a thickness essentially the same as that of the geometric physiologically functional features 116. In this embodiment, after vacuum deposition of the layer 120, the geometric physiologically functional features 116 of the sacrificial layer 114 are removed, for example, by chemical etching, photo etching, laser ablation, or other method reveal geometric physiologically functional features 122 patterned across the surface 104 of the implantable material 100. Each of the geometric physiologically functional features 122 is a recess that has a thickness or depth between a surface 124 of the layer 120 and the surface 104.

The shape of the recesses 122 as seen looking in the direction of arrow 126 in FIG. 12B may be any of the shapes described for the geometric physiologically functional features including: circle, square, rectangle, triangle, polygonal, hexagonal, octagonal, elliptical, parallel lines and intersecting lines, or any combination thereof. The recesses 122 may have the width 112, or diameter if the recesses 122 are circular, in a range between about 1 nanometer and about 75 micrometers, alternatively between about 1 nanometer and about 50 micrometers, alternatively between about 1 nanometer and about 2000 nanometers, or alternatively between about 1 nanometer and about 200 nanometers. Adjacent recesses 122 may be spaced apart by the distance D in a range from about 1 nanometer to about 20 micrometers, from about 1 nanometer to about 10 micrometers, from about 1 nanometer to about 5 micrometers, or from about 1 nanometer to about 3 micrometers. The distance D may be less than, about equal to or greater than the width 112. In another embodiment (not shown), the width 112 of each of the recesses 122 and/or the distance D between adjacent recesses 122 may vary in size to form a patterned array of the recesses 122.

Figure 13A:
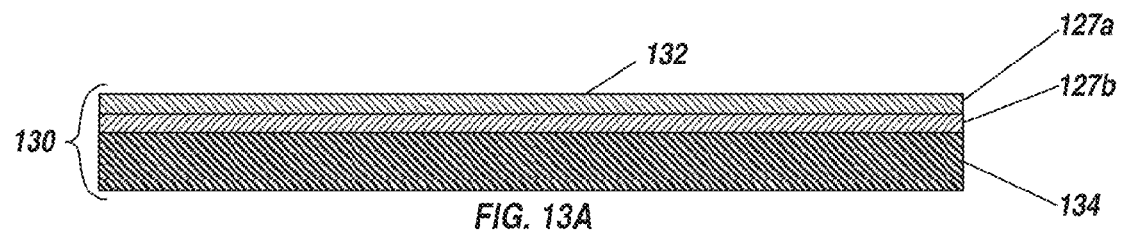
FIG. 13A illustrates a cross-sectional view of layers of vacuum deposited material deposited over a bulk material.

In another embodiment, the recesses 122 having width and spacing as described hereinabove with regard to FIGS. 12A and 12B may be formed by machining the recesses 122 through a layer or layers 128 of vacuum deposited material. For example, an implantable material 130 having a surface 132, may comprise a bulk material 134, the one or more layers 128 of vacuum deposited material, or the bulk material 134 and the one or more layers 128 of vacuum deposited material, as illustrated in FIG. 13A.

Figure 12C:
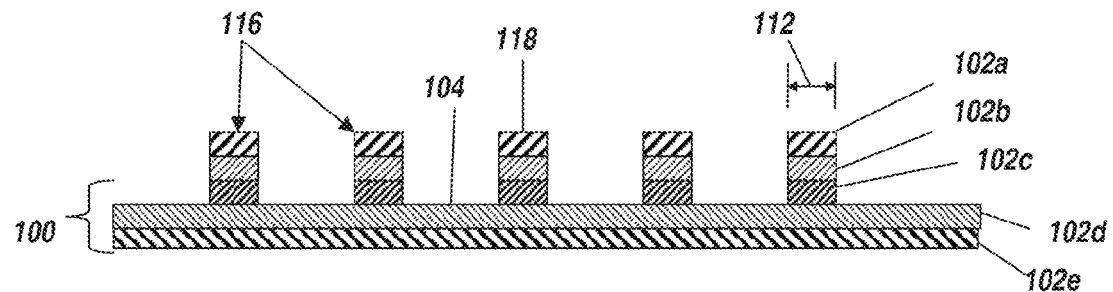

Alternatively, as shown in FIG. 12C, the geometric physiologically functional features 116 themselves include a plurality of deposited layers, wherein the geometric physiologically functional features 116 include the first layer 102a, the second layer 102b, and the third layer 102c. The geometric physiologically functional features 116 are deposited through a mask as previously indicated, on top of structural material of the stent or other medical device include deposited layer 102d and 102e. Alternatively, the geometric physiologically functional features 116 include the first layer 102a and the second layer 102b, deposited through the mask whereby the structural material of the stent or other medical device includes the layers 102c-102d. Alternatively, the geometric physiologically functional features 116 include the first layer 102a, the second layer 102b, the third layer 102c, and the fourth layer 102d, whereby the structural material of the stent or other medical device includes the fifth layer 102e. When additional layers 102a-102d are included in the geometric physiologically functional feature 116, the thickness of the layers as deposited can be modified to be a narrower or decreased thickness as to allow for the geometric physiologically functional feature 116 to be adjusted to a particular thickness. The layers of different vacuum deposited materials can be deposited to create the elevated surfaces having inherently different material properties. Alternatively, layers of the same vacuum deposited material can be deposited having differences in grain size, grain phase, and/or surface topography or variations of hydrophobic, hydrophilic or surface energy difference relative to the surface of the stent or structural material. The grain size, grain phase, and/or surface topography or variations of hydrophobic, hydrophilic or surface energy difference relative to the surface of the stent or structural material may be formed or included on the surface as shown in U.S. patent application Ser. No. 12/428,981, which was filed Apr. 23, 2009, incorporated by reference herein.

Figure 12D:
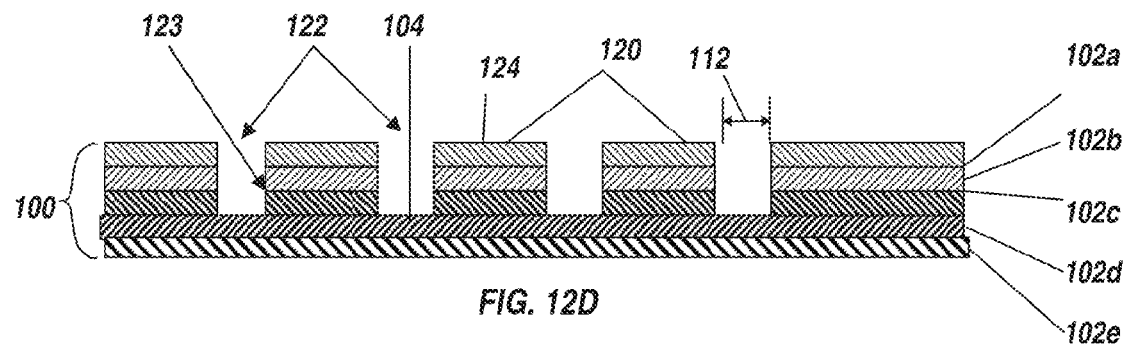

Alternatively, as shown in FIG. 12D, the recesses 122 may include a plurality of layers 102 to provide for differences in grain size, grain phase, and/or surface topography or variations of hydrophobic, hydrophilic or surface energy difference relative to the surface of the stent or structural material. The recesses 122 may be formed by the surface 124 being deposited through a mask as to form the layer 120 that gives rise to the plurality of recesses 122 with a wall 123. As such, the recesses 122 include an inner wall 123 including the first layer 102a, the second layer 102b, and the third layer 102c, whereby the surface 104 is on layer 102d, which is exposed on the bottom of the recess 122 and surface 124 is on top of layer 102a. Alternatively, the recesses 122 may include a wall of the first layer 102a and the second layer 102b, whereby the surfaces 124 are deposited through a mask, and the structural material of the stent or other medical device includes the layers 102d-102e. Alternatively, the recesses 122 include a wall of the first layer 102a, the second layer 102b, the third layer 102c, and the fourth layer 102d, and surfaces 124 are deposited through a mask whereby surface 102e that acts as the surface 104 of the structural material of the medical device. When additional layers 102a-102d are included as the wall in the geometric physiologically functional feature 116, the thickness of the layers as deposited can be modified to be a narrower or decreased thickness as to allow for the geometric physiologically functional feature 116 to be adjusted to a particular thickness. The layers of different vacuum deposited materials can be deposited to create recesses having inherently different material properties. Alternatively, layers of the same vacuum deposited material can be deposited having differences in grain size, grain phase, and/or surface topography or variations of hydrophobic, hydrophilic or surface energy difference relative to the surface of the stent or structural material.

Figure 13B:
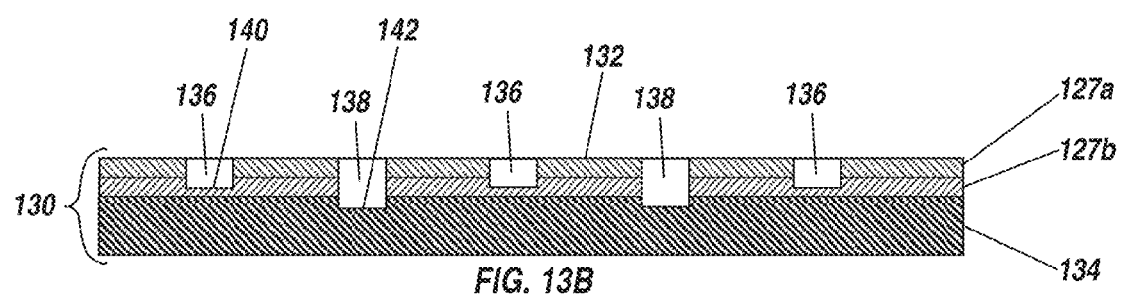
FIG. 13B illustrates recesses machined to various depths through a surface of the layers of material.

Referring to FIG. 13B, recesses 136 may be machined into the surface 132 of the implantable material 130 to have a depth greater than a thickness of a first layer of material 128a or recesses 138 may be machined into the surface 132 of the implantable material 130 to have a depth greater than a thickness of the first and second layers 128a, 128b of material. Two layers are illustrated for convenience of explanation and illustration; however, any number of layers 128 of material may be used as desired or appropriate. In this embodiment, each of the recesses 136 has a thickness or depth between the surface 132 of the layer 128a and a surface 140 that is within a second layer 128b. Similarly, each of the recesses 138 has a thickness or depth between the surface 132 of the layer 128a and a surface 142 that is within the bulk material 134.

Figure 11E:
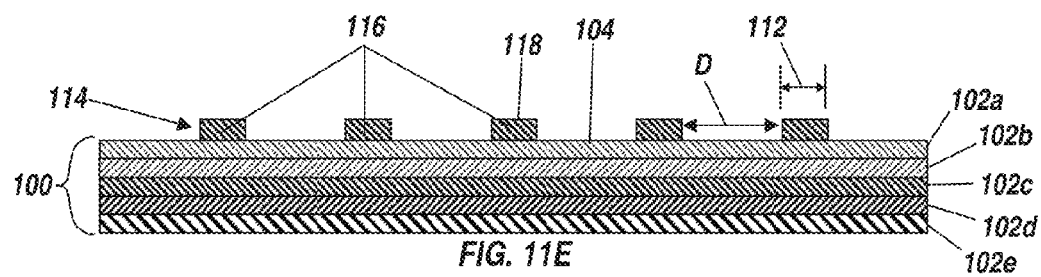
FIG. 11E illustrates a cross-sectional view of geometric physiologically functional features patterned across the surface of FIG. 11B.

An implantable material including geometric physiologically functional features comprising a layer or layers of vacuum deposited material, as illustrated by the geometric physiologically functional features 116 in FIG. 11E, recesses disposed through one or more layers of vacuum deposited material, as illustrated by the recesses 122 in FIG. 12B or the recesses 136 or 138 in FIG. 13B, has an inherently different structure than a block of material having recesses cut into it. The reason for this inherent difference lies in the differences in the materials making up surfaces exposed by the recesses. For example, in the case of a block of material and assuming that the block material is uniform in regard to material properties, an undisturbed surface of the block and a surface within a recess or groove cut into the block have the same material properties.

In contrast, layers of different vacuum deposited materials can be deposited to create recessed and/or elevated surfaces having inherently different material properties. In fact, layers of the same vacuum deposited material can be deposited having differences in grain size, grain phase, and/or surface topography. The alternative grain size, grain phase, and/or surface topography may be included or formed, by way of example, any of the methods disclosed in commonly assigned U.S. patent application Ser. No. 12/428,981, filed Apr. 23, 2009, incorporated by reference herein. For example, surfaces of the recesses 122, 136 can be deposited to have a roughened surface topography and a large grain size and surfaces of the material deposited defining the recesses 122, 136, for example the layer 120 illustrated in FIG. 12B, can have a relatively smoother surface topography and/or a smaller grain size. Alternative grain sizes and surfaces may be formed and included as shown in U.S. patent application Ser. No. 12/428,981, which was filed Apr. 23, 2009, previously incorporated by reference.

It is contemplated that a factor in increasing endothelialization of a surface of an implanted medical device may be the cleanliness of the surface. In this context, cleanliness refers to the presence or lack of contaminant molecules bonding to otherwise unsaturated chemical bonds at the surface. A perfectly clean surface, for example as may exist in a vacuum, comprises unsaturated bonds at the surface that have not bound to any contaminant molecules. The unsaturated bonds provide the surface with a higher surface energy as compared to a contaminated surface having fewer unsaturated bonds, which have a lower surface energy. Measurements of surface energy may be accomplished by contact angle measurements, as disclosed in U.S. patent application Ser. No. 12/428,981, which was filed Apr. 23, 2009.

Unfortunately, unsaturated chemical bonds at the surface will bond to contaminant molecules when exposed thereto. For example, there are many air-borne chemistries such as phthalates, hydrocarbons, and even water that may bond to unsaturated bonds or otherwise attach to reactive spots such as, for example, residual negative charges on the surface of a metal oxide. Such contaminant molecules, for example, normally occurring hydrocarbons, $SO_2$, NO, etc., occupy otherwise unsaturated bonds thereby reducing the number of unsaturated bonds and lowering the surface energy of the surface. Such reduction in the number of unsaturated bonds decreases the availability of such unsaturated bonds for interaction with blood proteins.

The air atmosphere around the surface include normally occurring impurities which will be attracted to the unsaturated chemical bonds at levels in the air around 1×109 to 1×106 so it will take a few seconds before the surface is contaminated by their Brownian motion, after 1 min, most of the unsaturated bond are saturated with contaminants. One molecular monolayer (i.e. a single layer of molecules) will be adsorbed on the surface. On longer time scales, additional molecules may bond to the surface and build multi-layers of contaminant molecules. The surface of a few molecular monolayers of contaminants may have thickness of about 0.1-2 nm, which may be detected by sensitive surface analysis as indicated above.

Thus, as relates to endothelialization, a cleaner surface having more unsaturated bonds provides increased potential for interaction with blood proteins. It is contemplated that a contaminated surface of a vacuum deposited or bulk material can be activated, or made more likely to interact with blood proteins, by removing the contaminant molecules that occupy the otherwise unsaturated bonds at the surface. There may be several techniques for accomplishing such activation, including by way of example and not limitation, chemical etching, wet chemical etching, oxidation, electrochemical treatment, thermal treatment, UV-ozone cleaning, coating by evaporation or sputtering, etc. For example, another technique for activating a vacuum deposited surface may be by using plasma electron bombardment under vacuum, a technique also known as plasma etching. The contaminant layer may be detected by surface-sensitive spectrosscopies, such as Auger electron spectroscopy (AES), x-ray photoemission spectroscopy (XPS or ESC), infrared reflection absorption spectroscopy (IRAS, FT-IR, etc.) secondary ion mass spectroscopy (SIMS), and those disclosed in U.S. patent application Ser. No. 12/428,981.

Plasma etching the sample to be treated is positioned within a controlled electrical gas discharge (a plasma). The plasma may be formed by applying a high voltage (AC or DC) over a gas under considerably lower pressure than one atmosphere (typically 0.1-1 mm Hg, or a vacuum). Because of the low pressure and because gas purity is vital for the process, the discharge and the sample must be housed in a hermetically closed system that can be evacuated by vacuum pumps, and whose gas composition can be controlled. The plasma also has sufficient energy and momentum to remove atoms and molecules that are adsorbed on unsaturated bonds, or are constituents of the native surface. As such, the contamination layer bond to unsaturated bonds may be removed, to recreate the unsaturated bonds on the surface and thus increasing the surface energy. Depending on the parameters of the discharge (gas pressure and composition, applied voltage, current density, position of the sample, etc.) the surface treatment can be mild (mainly removal of the contamination layer) or more aggressive. The complete surface oxide layer on a metal may be removed so that the bare metal is exposed. The latter occurs only provided that no oxidizing or other reactive gases are present, i.e., the used gas must be a noble gas such as Ar, Kr, or Xe. By controlling the gas atmosphere, the composition of the newly formed surface is controlled; if oxygen is added, oxide will be formed; if nitrogen or hydrocarbons are added, surface nitride or surface carbide, respectively, will form, etc. The gas purity must be high, as impurities within the gas will react to the high energy cleaned surfaces.

Because of the omnipresence of contaminant molecules in the environment, a surface once activated may not remain activated until implantation into a patient. Thus, an important consideration of the activation process is how to preserve the activated surface long enough to provide the benefit of activation upon implantation. In this context, the activated surface may be preserved by introducing a contaminant gas or liquid into the plasma etching process in a controlled manner, which may be easily removed before use of the medical device. The contaminant layer may be a known biodegradable material or may be a contaminant layer or coating of inorganic or organic nature or a mixture of both. For example, the contaminant layer may be layer readily removed by a saline or water solution, which are typically used in flushing procedures or washing procedures.

Alternatively, the activated surface may be coated with a protective coating, for example, a biodegradable material that dissolves upon exposure to the in vivo environment when implanted. The biodegradable material may alternatively be dissolved via introduction of an externally delivered fluid solvent during implantation. Alternatively, the protective coating may be a fluid in which the activated device is immersed until implantation. For example, it is contemplated that storing the activated surface in water facilitates preservation of the activation as compared to exposure of the activated surface to air. The biodegradable material may be any material, natural or synthetic, that may be broken down by living organisms, including, but not limited to a biodegradable organic substance, biodegradable polymer substances (Poly(lactic acid) PLA, poly(L-lactic acid) (PLLA), poly(lactic-co-glycolic acid) PLGA, poly(glycolicacid) (PGA), Polyethylene glycol, PEG, polytetrafluoroethylene (PTFE), and the like), peptides or proteins, carbohydrates, nucleic acids, fatty acids, carbon-containing compounds, nanoparticles, microparticles, biocomposites, sol-gel coatings, hydrogels water-soluble bioactive agent and poly(alkyl cyanoacrylate) polymer coating; nanoparticle coating formed by electrospraying; a poly(diol citrates)-based coatings; natural biodegradable hydrophobic polysaccharides coatings, hydrophilic polymers, and the like. Alternatively, other materials may be used, such as gold, other metals, heparin, silicon carbide, titanium-nitride-oxide, phoshphorylcholine, and other medical device coatings.

The method disclosed herein comprehends the creation of a patterned array of geometric physiologically functional features elevated relative to a surface of an implantable biocompatible material, recessed relative to the surface, or disposed on the surface. For example, in accordance with an alternative embodiment, the implantable biocompatible material is formed of a bulk material of titanium, nickel-titanium alloy or other titanium-rich alloy metals or a top most layer of titanium, nickel-titanium alloy or other titanium-rich alloy metals deposited over the bulk material. The titanium, nickel-titanium alloy or other titanium-rich alloy metal is oxidized to convert surface titanium to titanium dioxide, then covered with a pattern-mask and exposed to high intensity UV irradiation. It is well-known that titanium dioxide ($TiO_2$) absorbs UV radiation and has been used in a variety of applications as a UV inhibitor to prevent UV transmission across a $TiO_2$ barrier layer. It has been discovered that upon exposure to UV irradiation, an originally hydrophobic and oleophilic titanium oxide layer becomes amphiphilic.

The effect of UV irradiation on a titanium oxide surface is believed to occur because of unsymmetrical cleavage of the Ti—O bond to leave $Ti^{3+}$ ions on the surface in some regions. Presently, these amphiphilic surfaces are being used in a range of technological applications, such as self-cleaning paints and anti-misting glasses. It has been recognized that these amphiphilic titanium oxide layers have use in medical applications. Zarbakhsh, A., *Characterization of photon-controlled titanium oxide surfaces*, ISIS Experimental Report, Rutherford Appelton Laboratory, May 16, 2000 (which may be found on the internet at: www.isis.rl.ac.uk/isis2001/reports/11144.pdf).

The amphiphilic state of the UV irradiated titanium oxide may be advantageously employed as an alternative to depositing patterned elevated or recessed geometric physiologically functional features onto the implantable biocompatible material. An implantable biocompatible material fabricated having a bulk substrate or a top most vacuum deposited layer of titanium or a titanium alloy is masked with a pattern mask having a plurality of openings passing there through. As with the above-described embodiment, the plurality of openings preferably have a size and special array selected to define affinity binding domains and cellular migration cites for promoting endothelial cell binding and proliferation across the substrate surface.

The open surface area of each of the plurality of openings in the pattern mask is preferably in the range of between about 1 nm to about 75 μm, and with adjacent pairs of openings being in a spaced apart relationship such that a distance of about 1 nm to about 75 μm exists between the openings, the inter-opening being greater than, about equal to, or less than the size of the opening. By interposing the pattern mask between a UV source and the surface of the implantable biocompatible material, a pattern of UV irradiated regions is imparted to the surface implantable biocompatible material, thereby altering the titanium dioxides present at the irradiated regions and forming affinity domains at the surface implantable biocompatible material.

Figure 10A:
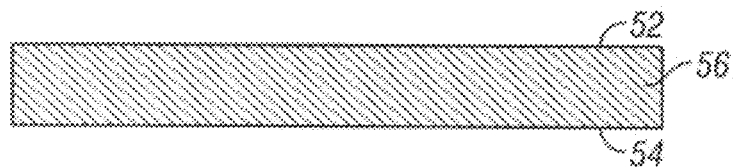
FIGS. 10A-10D are cross-sectional diagrammatic views of one embodiment, the combination of a-d representing the steps to make an inventive implantable material with chemically defined geometric physiologically functional features.

Referring to FIG. 10A, a portion of an implantable material 56 made of titanium or a titanium-alloy is shown having at least one surface 52 and 54 that is oxidized by heating or an equivalent known by the person skilled in the art.

Figure 10B:
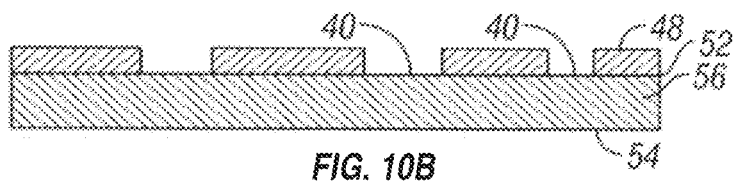

Referring to FIG. 10B, according to one embodiment, a machined mask 48 that had laser-cut holes 40 of defined size from about 1 nm to about 75 μm, from about 1 nm to about 50 μm, from about 1 nm to about 2000 nm, and preferably from about 1 nm to about 200 nm, patterned throughout to coat the at least one surface 52 of the implantable material 56 and is tightly adhered to the covered surface 52.

Figure 10C:
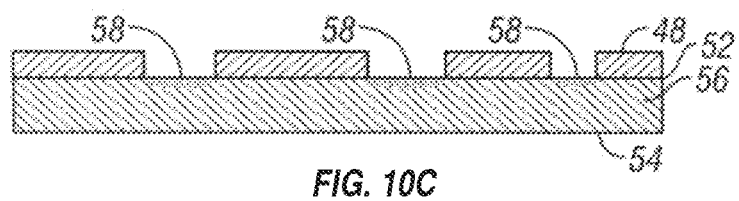

Referring to FIG. 10C, the implantable material 56 covered with the mask 48 is then illuminated by the ultraviolet rays. Because $TiO_2$ is sensitive to ultraviolet, the chemical composition in holes 58 is different from the area that is covered by the mask. In contrast to the geometric physiologically functional features illustrated in FIGS. 9C, 11E, 12B, and 13B, the geometric physiologically functional features 59 in FIG. 10C are not elevated and therefore have zero thickness relative to the surrounding surface of the implantable material.

Figure 10D:
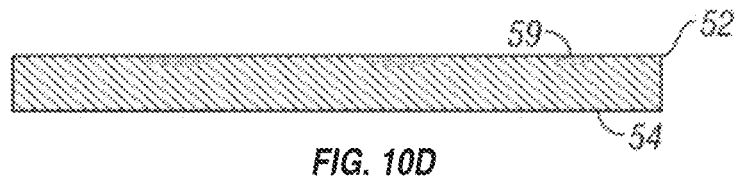

Referring to FIG. 10D, after ultraviolet irradiation, the mask is removed to reveal the surface 52 that surrounds the geometric physiologically functional features 59 formed by ultraviolet irradiation. As described above, because the shape of the holes 58 in the mask 48 could be in any of the shapes described for the geometric physiologically functional features including: circle, square, rectangle, triangle, parallel lines and intersecting lines, and combinations thereof, the geometric physiologically functional features 58 accordingly adopts such shapes also.

Example 1

Nickel-titanium sheets were heated to oxidize titanium present at the surface of the sheet. Pattern masks fabricated from machined metal were laser drilled a pattern of holes having diameters ranging from 15 μm to 50 μm, with a single diameter of holes on each pattern mask. A single pattern mask was placed over a single nickel-titanium sheet and the assembly was exposed to high intensity ultra-violet irradiation. After UV irradiation, the irradiated nickel-titanium sheet was placed on a fully endothelialized test surface and maintained at 37° C. under simulated in vivo flow conditions and under static flow conditions. Qualitative observations were periodically made and it was found that endothelial cells bound to the pattern of UV irradiated affinity domains and migrated across the nickel-titanium sheet by proliferating across the pattern of affinity domains, eventually fully seeding endothelium on the nickel-titanium sheet.

Example 2

Selected metal pieces (Flat, 1×1 cm square pieces (1/16 in. thick) of electropolished 316L stainless steel, electropolished and heat-treated, electropolished Nitinol, gold and titanium) were subjected to radiofrequency plasma glow discharge using an EMS-100 glow discharge unit (Electron Microscopy Services, Fort Washington, Pa.). For this procedure, the flat metal piece is placed on a flat metal platform within the glow discharge vacuum chamber. The plasma treatments were conducted at a base vacuum pressure of 10-2 mbar in the presence of a purified argon gas atmosphere. The sample was always at negative potential as the cathode using an applied current of 20 mamps for the treatment time of 3 min. Under these conditions the surface of the sample is bombarded with argon ions resulting in the removal of surface oils and other surface contaminating molecules. Electrostatic force analyses were performed on these samples within 2 hr after removal from glow discharge treatment.

For calculation of metal surface energy values, contact angle measurements were performed using a VCA-2500XE video contact angle system (AST systems, Billerica, Mass.) on the flat metal pieces after cleaning as described above. The surface energy of all materials studied was determined by the advancing contact angle measurement of three standard liquids; water, formamide and xylene; on each metal surface and calculated by the harmonic mean method. Ten videocaptures per second of the advancing fluid droplet/solid interface were obtained for water and formamide and 65 captures per second for xylene. All experiments were repeated 4 times.

Figure 14:
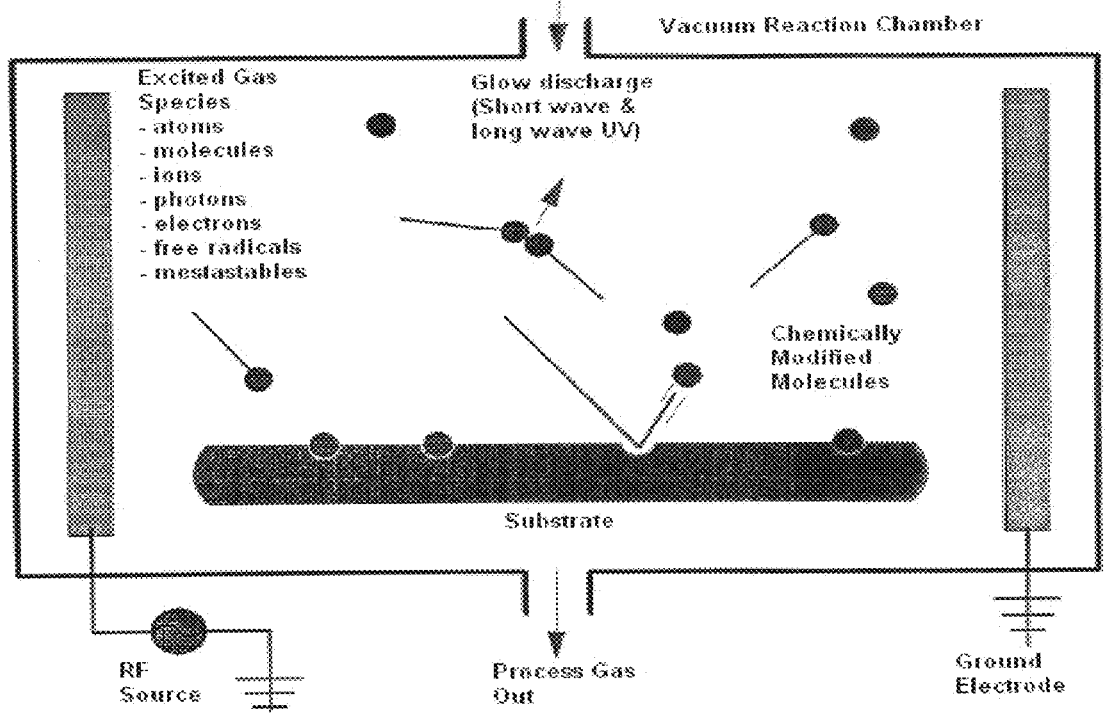
FIG. 14 is a graph of the mean electrostatic force measurements comparing 5 different metal surfaces; measurements were performed using a 5 nm silicon nitride tip in the presence of a 0.01 M. NaCl medium at pH 7.4; force measurement values for each metal represent the mean of data from five different samples on which 5 sites were analyzed using 10 measurements at each site; and mean values were compared using Student's unpaired t-analysis.
Figure 15:
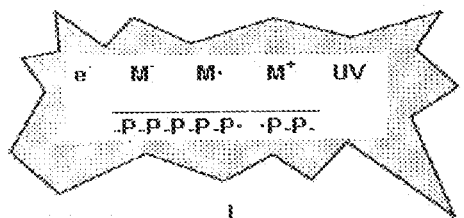
FIG. 15 is a graph of the correlation of mean electrostatic measurements on the different metal surfaces presented in FIG. 14 with the polar component of total metal surface energy; and total surface energy was calculated by the harmonic method from surface contact angle measurements using water, formamide and xylene as the test liquids.

Glow discharge plasma treatment is often used as a method of cleaning and removing surface contaminants from metallic as well as other surfaces. Glow discharge treatment of many metallic surfaces causes their surfaces to change from very hydrophobic surfaces on which water beads to a hydrophilic surface on which water rapidly spreads. This can be quantitatively measured using contact angle measurement techniques, described above. In the case of stainless steel, a change in water contact angle was measured from 98° prior to treatment to 7° after glow discharge. With this profound alteration in surface characteristics associated with glow discharge treatment, it was important to examine whether these physical alterations in surface behavior might be associated with an alteration in surface electrostatic forces. Gold, stainless steel and electropolished Nitinol all exhibit net attractive forces subsequent to glow discharge treatment, as shown in FIG. 14. Nitinol and gold now exhibit highly attractive forces that are significantly higher ($p<0.001$) than that observed on stainless steel.

Figure 16:
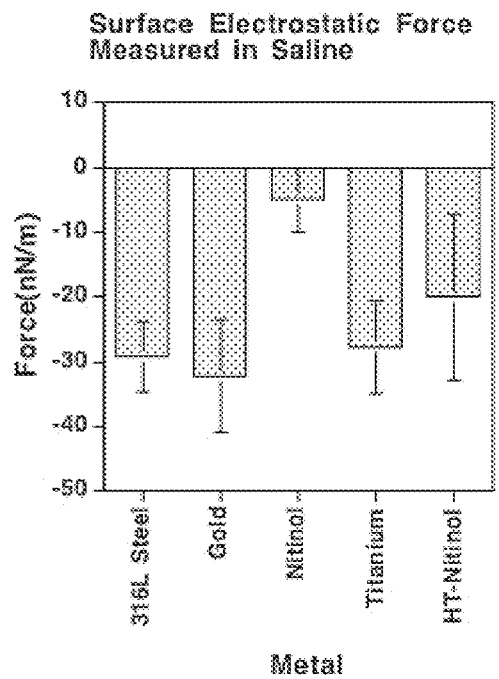
FIG. 16 is a graph showing significant correlation was observed between the polar component of total surface energy and AFM measured electrostatic force.
Figure 17:
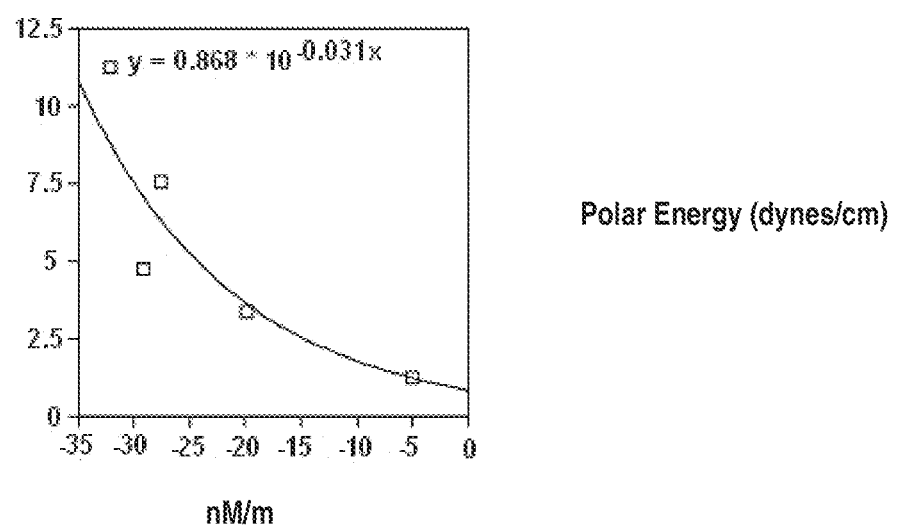
FIG. 17 is a graph showing that electropolished Nitinol exhibits the lowest polar energy component of all four surfaces and, furthermore, that when its surface becomes heavily oxidized that the polar component increases almost 3-fold (from 1.3 to 3.4 dynes/cm), again, paralleling changes observed in surface electrostatic force.

It is likely based upon the profound change in measured surface electrostatic energy associated with glow discharge treatment and a similar dramatic change in water contact angle measurements that the two approaches to surface characteristics might be fundamentally related. To fully explore this possibility, contact angles on gold, stainless steel, electropolished Nitinol, and heat-treated oxidized Nitinol were measured using water, xylene, and formamide. Using the Harmonic Mean method, these measurements were used to calculate the total surface energy associated with each of the metallic surfaces. The final total surface energy value represents the sum of the polar and hydrophobic dispersive forces. To evaluate a possible association with these components of total surface energy to AFM measured electrostatic forces, the possible correlations between electrostatic force and either total surface energy were examined, the polar component of surface energy or the dispersive component. As demonstrated in FIG. 16, a significant correlation was observed between the polar component of total surface energy and AFM measured electrostatic force. Within this comparison it is noteworthy that electropolished Nitinol exhibits the lowest polar energy component of all four surfaces and, furthermore, that when its surface becomes heavily oxidized that the polar component increases almost 3-fold (from 1.3 to 3.4 dynes/cm), again, paralleling changes observed in surface electrostatic force (FIG. 17).

While the present invention has been described with reference to its preferred embodiments, those of ordinary skill in the art will understand and appreciate that variations in materials, dimensions, geometries, and fabrication methods may be or become known in the art, yet still remain within the scope of the present invention which is limited only by the claims appended hereto. It is understood, therefore, that this disclosure is not limited to the particular embodiments disclosed, but it is intended to cover modifications that may include a combination of features illustrated in one or more embodiments with features illustrated in any other embodiments. Various modifications, equivalent processes, as well as numerous structures to which the present disclosure may be applicable will be readily apparent to those of skill in the art to which the present disclosure is directed upon review of the present specification. Accordingly, this description is to be construed as illustrative only and is presented for the purpose of enabling those skilled in the art to make and use the implantable materials having engineered surfaces described herein and to teach the best mode of carrying out the same.

I claim:

1. A method for making an implantable, biocompatible material, comprising the steps of:
   a. providing an implantable, biocompatible material having at least one surface intended to contact tissue and body fluids in vivo;
   b. providing a mask having a defined pattern of openings corresponding in size and spacing to a predetermined distribution of endothelial cell binding domains to be imparted to the at least one surface;
   c. treating the at least one surface of the biocompatible material through the mask by at least one of:
      i. vacuum depositing a layer of material onto the at least one surface, wherein the vacuum deposited layer is different from the at least one surface immediately therebeneath in a material property selected from the group of material properties consisting of: grain size, grain phase, grain material composition, surface topography, and transition temperature, and removing the mask to yield a plurality of binding domains defined on the at least one surface of the implantable, biocompatible material; and
      ii. vacuum depositing a layer of sacrificial material onto the at least one surface, removing the mask from the at least one surface, vacuum depositing a second layer of material onto the at least one surface, wherein the second vacuum deposited layer is different from the at least one surface immediately therebeneath in a material property selected from the group of material properties consisting of: grain size, grain phase, grain material composition, surface topography, and transition temperature, and removing the sacrificial material to yield a plurality of binding domains defined on the at least one surface of the implantable, biocompatible material.

2. The method of claim 1, wherein the implantable, biocompatible material in the providing step comprises a bulk material.

3. The method of claim 1, wherein the implantable, biocompatible material in the providing step comprises one or more layers of vacuum deposited biocompatible materials.

4. The method of claim 1, wherein a gap distance measured between immediately adjacent openings in the mask measures between about 1 nanometer and about 2000 nanometers, wherein the gap distance measures about the same as a width of each of the openings, and wherein the mask has a thickness between about 1 nm and about 3 μm.

5. The method of claim 1, further including the step of activating the at least one surface of the implantable, biocompatible material by removing contaminant molecules that occupy otherwise unsaturated bonds at the at least one surface.

6. The method of claim 5, wherein the activating step further comprises activating the at least one surface of the implantable, biocompatible material by a technique for activation selected from the techniques for activation of the at least one surface consisting of: chemical etching, electrochemical treatment, thermal treatment, and plasma etching.

7. The method of claim 5, further including the step of preserving the activation of the at least one surface prior to implantation.

8. The method of claim 7, wherein the preserving step further includes coating the activated at least one surface subsequent to activation thereof with a biodegradable material that dissolves upon exposure to an in vivo environment.

9. The method of claim 7, wherein the preserving step further includes coating the activated at least one surface subsequent to activation thereof with a biodegradable material.

* * * * *